US010624704B2

(12) United States Patent
Farritor et al.

(10) Patent No.: US 10,624,704 B2
(45) Date of Patent: Apr. 21, 2020

(54) ROBOTIC DEVICES WITH ON BOARD CONTROL AND RELATED SYSTEMS AND DEVICES

(71) Applicant: Board of Regents of the University of Nebraska, Lincoln, NE (US)

(72) Inventors: Shane Farritor, Lincoln, NE (US); Erik Mumm, Longmont, CO (US); Philip Chu, Friendswood, TX (US); Nishant Kumar, Bergenfield, NJ (US); Jason Dumpert, Omaha, NE (US); Yutaka Tsutano, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 229 days.

(21) Appl. No.: 15/661,147

(22) Filed: Jul. 27, 2017

(65) Prior Publication Data
US 2018/0071036 A1    Mar. 15, 2018

Related U.S. Application Data

(63) Continuation of application No. 13/573,849, filed on Oct. 9, 2012, now Pat. No. 9,770,305.
(Continued)

(51) Int. Cl.
*A61B 34/30* (2016.01)
*A61B 17/00* (2006.01)
*A61B 34/00* (2016.01)
*A61B 17/29* (2006.01)
*A61B 34/37* (2016.01)
(Continued)

(52) U.S. Cl.
CPC ........ *A61B 34/30* (2016.02); *A61B 17/00234* (2013.01); *A61B 17/29* (2013.01); *A61B 34/00* (2016.02); *A61B 34/37* (2016.02); *A61B 90/30* (2016.02); *A61B 90/361* (2016.02); *A61B 2017/2906* (2013.01); *A61B 2034/302* (2016.02); *A61B 2217/005* (2013.01); *A61B 2217/007* (2013.01)

(58) Field of Classification Search
CPC ...................................................... A61B 34/30
USPC .................................................. 318/560, 561
See application file for complete search history.

(56) References Cited

U.S. PATENT DOCUMENTS 3,870,264 A    3/1975  Robinson
3,989,952 A    11/1976 Timberlake et al.
(Continued)

FOREIGN PATENT DOCUMENTS

CN    102821918    12/2012
DE    102010040405    3/2012
(Continued)

OTHER PUBLICATIONS

Franzino, "The Laprotek Surgical System and the Next Generation of Robotics," Surg Clin North Am, 2003 83(6): 1317-1320.
(Continued)

*Primary Examiner* — David Luo
(74) *Attorney, Agent, or Firm* — Davis, Brown, Koehn, Shors & Roberts, P.C.; Sean D. Solberg

(57) ABSTRACT

The embodiments disclosed herein relate to various medical device components, including components that can be incorporated into robotic and/or in vivo medical devices. Certain embodiments include various modular medical devices for in vivo medical procedures.

19 Claims, 41 Drawing Sheets

Related U.S. Application Data

(60) Provisional application No. 61/680,809, filed on Aug. 8, 2012.

(51) Int. Cl.
  *A61B 90/30* (2016.01)
  *A61B 90/00* (2016.01)

(56) References Cited

U.S. PATENT DOCUMENTS

| | | |
|---|---|---|
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyake |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,172,639 A | 12/1992 | Wiesman et al. |
| 5,195,388 A | 3/1993 | Zona et al. |
| 5,201,325 A | 4/1993 | McEwen et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,436,542 A | 7/1995 | Petelin et al. |
| 5,441,494 A | 8/1995 | Ortiz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyaman et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |

(56) References Cited

U.S. PATENT DOCUMENTS

| | | |
|---|---|---|
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tiemey et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,155,316 B2 * | 12/2006 | Sutherland ............ A61B 90/25 700/248 |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,353,897 B2 | 1/2013 | Doyle et al. |
| 9,089,353 B2 | 7/2015 | Farritor et al. |
| 2001/0018591 A1 | 8/2001 | Brook et al. |

(56) References Cited

U.S. PATENT DOCUMENTS

| | | |
|---|---|---|
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zadno-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Manzo et al. |
| 2010/0245549 A1 | 9/2010 | Allen et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0020779 A1 | 1/2011 | Hannaford et al. |
| 2011/0071347 A1 | 3/2011 | Rogers et al. |

(56) References Cited

U.S. PATENT DOCUMENTS

| | | |
|---|---|---|
| 2011/0071544 A1 | 3/2011 | Steger et al. |
| 2011/0098529 A1 | 4/2011 | Ostrovsky et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0253515 A1 | 10/2012 | Coste-Maniere et al. |
| 2013/0131695 A1 | 5/2013 | Scarfogliero et al. |
| 2013/0345717 A1 | 12/2013 | Markvicka et al. |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0303434 A1 | 10/2014 | Farritor et al. |
| 2015/0051446 A1 | 2/2015 | Farritor et al. |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| JP | 05-115425 | 5/1993 |
| JP | 2006508049 | 9/1994 |
| JP | 07-016235 | 1/1995 |
| JP | 07-136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2003220065 | 8/2003 |
| JP | 2004144533 | 5/2004 |
| JP | 2004-180781 | 7/2004 |
| JP | 2004322310 | 11/2004 |
| JP | 2004329292 | 11/2004 |
| JP | 2006507809 | 3/2006 |
| JP | 2010536436 | 8/2007 |
| JP | 2009106606 | 5/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 1/2006 |
| WO | 2006079108 | 7/2006 |
| WO | 2007011654 | 1/2007 |
| WO | 2007111571 | 10/2007 |
| WO | 2007149559 | 12/2007 |
| WO | 2009023851 | 2/2009 |
| WO | 2009144729 | 12/2009 |
| WO | 2010050771 | 5/2010 |
| WO | 2011075693 | 6/2011 |
| WO | 2011118646 | 9/2011 |
| WO | 2011135503 | 11/2011 |
| WO | 2013009887 | 1/2013 |
| WO | 2014011238 | 1/2014 |

OTHER PUBLICATIONS

Franklin et al., "Prospective Comparison of Open vs. Laparoscopic Colon Surgery for Carcinoma: Five-Year Results," Dis Colon Rectum, 1996; 39: S35-S46.

Flynn et al., "Tomorrow's surgery: micromotors and microrobots for minimally invasive procedures," Minimally Invasive Surgery & Allied Technologies, 1998; 7(4): 343-352.

Fireman et al., "Diagnosing small bowel Crohn's desease with wireless capsule endoscopy," Gut 2003; 52: 390-392.

Fearing et al., "Wing Transmission for a Micromechanical Flying Insect," Proceedings of the 2000 IEEE International Conference to Robotics & Automation, Apr. 2000; 1509-1516.

Faraz et al., "Engineering Approaches to Mechanical and Robotic Design for Minimaly Invasive Surgery (MIS)," Kluwer Academic Publishers (Boston), 2000, 13pp.

Falcone et al., "Robotic Surgery," Clin. Obstet. Gynecol. 2003, 46(1): 37-43.

Fraulob et al., "Miniature assistance module for robot-assisted heart surgery," Biomed. Tech. 2002, 47 Suppl. 1, Pt. 1: 12-15.

Fukuda et al., "Mechanism and Swimming Experiment of Micro Mobile Robot in Water," Proceedings of the 1994 IEEE International Conference on Robotics and Automation, 1994: 814-819.

Fukuda et al., "Micro Active Catheter System with Multi Degrees of Freedom," Proceedings of the IEEE International Conference on Robotics and Automation, May 1994, pp. 2290-2295.

Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.

Dumpert et al., "Improving in Vivo Robot Visioin Quality," from the Proceedings of Medicine Meets Virtual Realtiy, Long Beach, CA, Jan. 26-29, 2005. 1 pg.

Dakin et al., "Comparison of laparoscopic skills performance between standard instruments and two surgical robotic systems," Surg Endosc., 2003; 17: 574-579.

Cuschieri, "Technology for Minimal Access Surgery," BMJ, 1999, 319: 1-6.

Grady, "Doctors Try New Surgery for Gallbladder Removal," The New York Times, Apr. 20, 2007, 3 pp.

Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.

Canthasopeephan et al., (2003), "Measuring Forces in Liver Cutting: New Equipment and Experimenal Results," Annals of Biomedical Engineering 31: 1372-1382.

Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.

Guber et al., "Miniaturized Instrument Systems for Minimally Invasive Diagnosis and Therapy," Biomedizinische Technic. 2002, Band 47, Erganmngsband 1: 198-201.

Abbott et al., "Design of an Endoluminal Notes Robotic System," from the Proceedings of the 2007 IEEE/RSJ Int'l Conf. on Intelligent Robot Systems, San Diego, CA, Oct. 29-Nov. 2, 2007, pp. 410-416.

Allendorf et al., "Postoperative Immune Function Varies Inversely with the Degree of Surgical Trauma in a Murine Model," Surgical Endoscopy 1997; 11:427-430.

Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.

Atmel 8005X2 Core, http://www.atmel.com, 2006, 186pp.

(56) References Cited

OTHER PUBLICATIONS

Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughliin, M.L, Hespanha, J.P., and Sukhatme, G., editors. Touch in virtual environments, IMSC Series in Multimedia 2001, 28pp.
Dumpert et al., "Stereoscopic in Vivo Surgical Robots," IEEE Sensors Special Issue on In Vivo Sensors for Medicine, Jan. 2007, 10 pp.
Green, "Telepresence Surgery", Jan. 1, 1995, Publisher: IEEE Engineering in Medicine and Biology.
Cleary et al., "State of the Art in Surgical Rootics: Clinical Applications and Technology Challenges", "Computer Aided Surgery", Jan. 1, 2002, pp. 312-328, vol. 6.
Stoianovici et al., "Robotic Tools for Minimally Invasive Urologic Surgery", Nov. 1, 2002, pp. 1-17.

\* cited by examiner

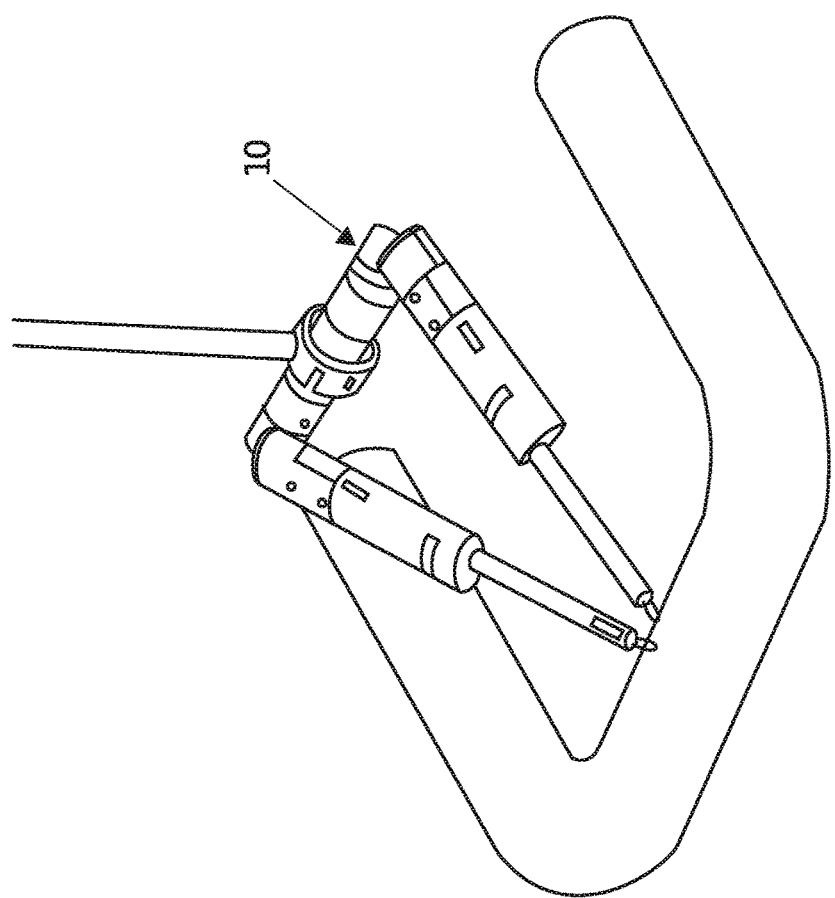

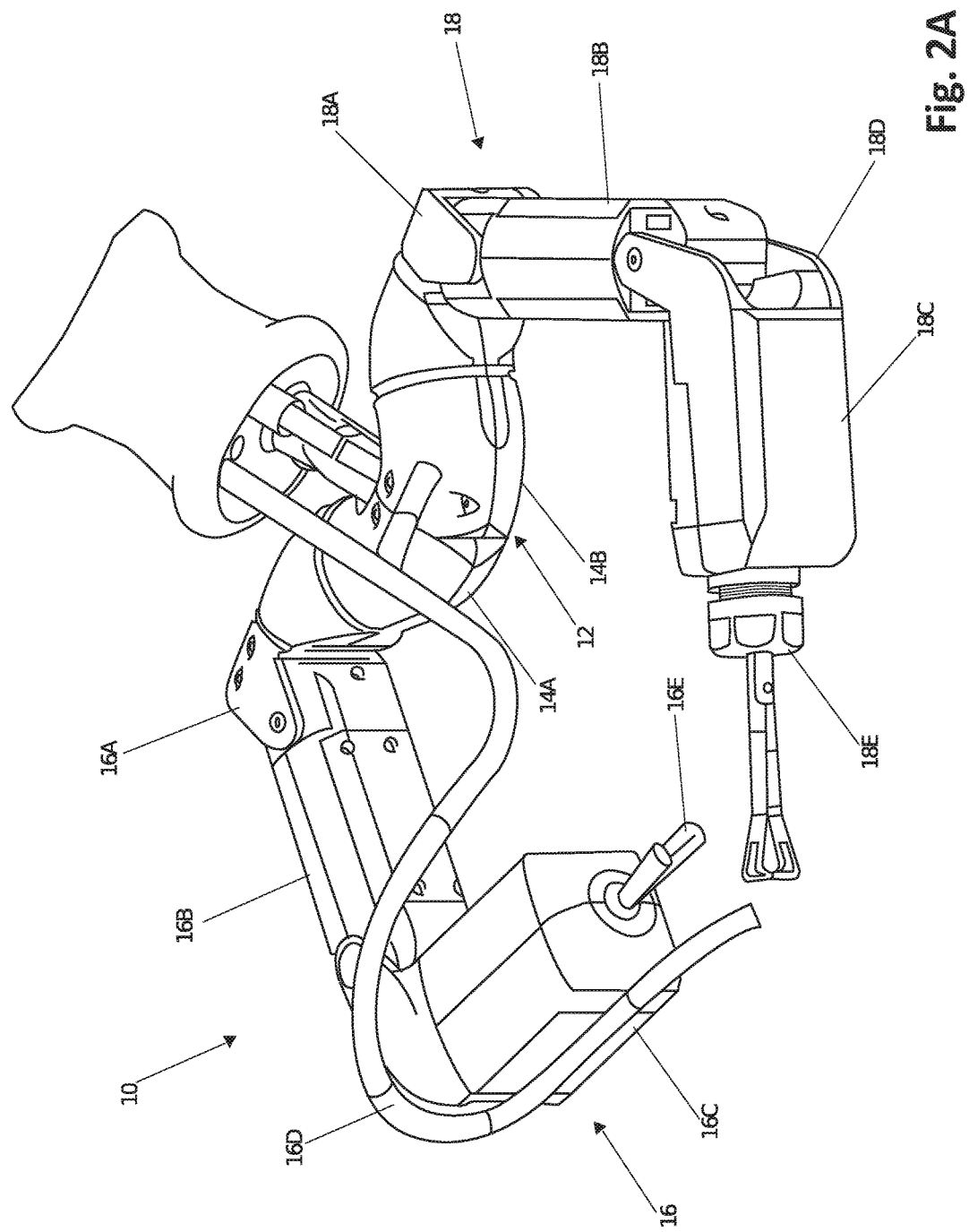

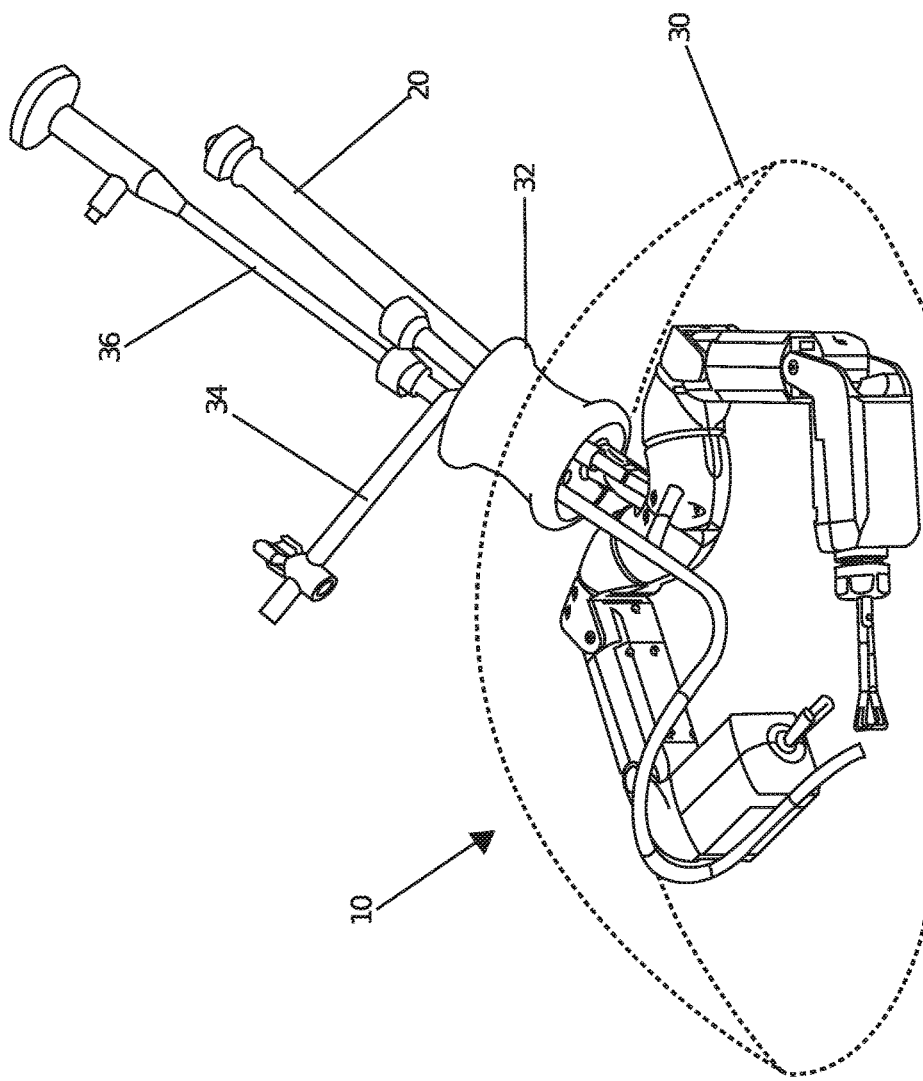

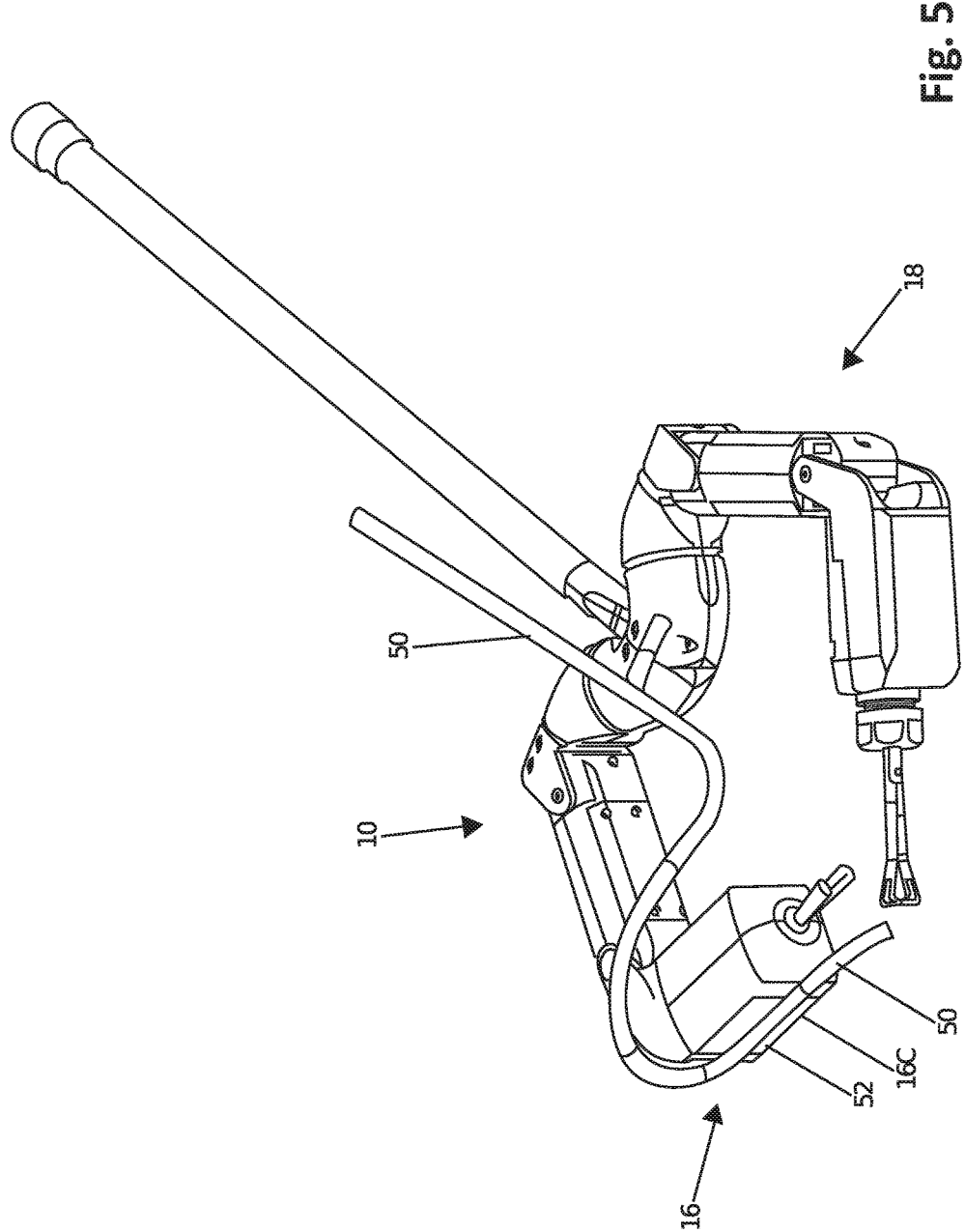

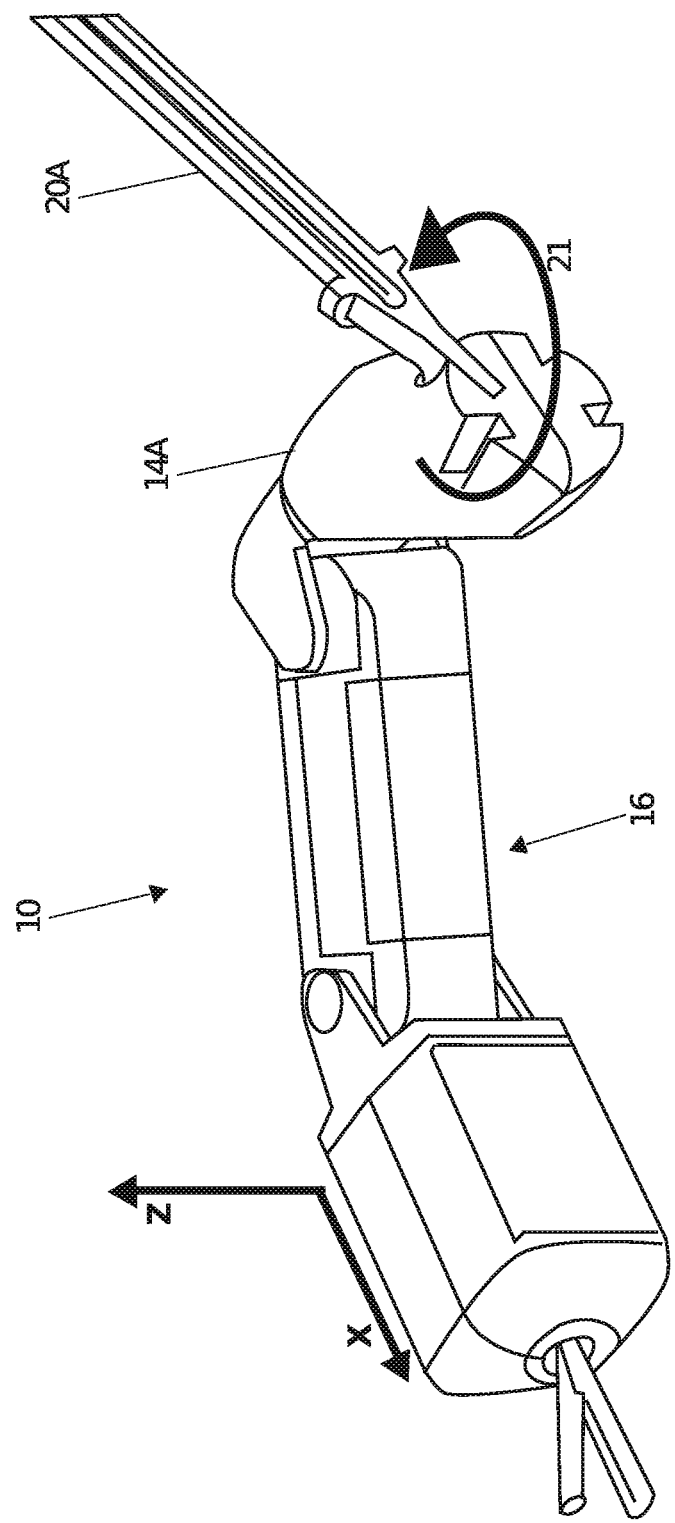

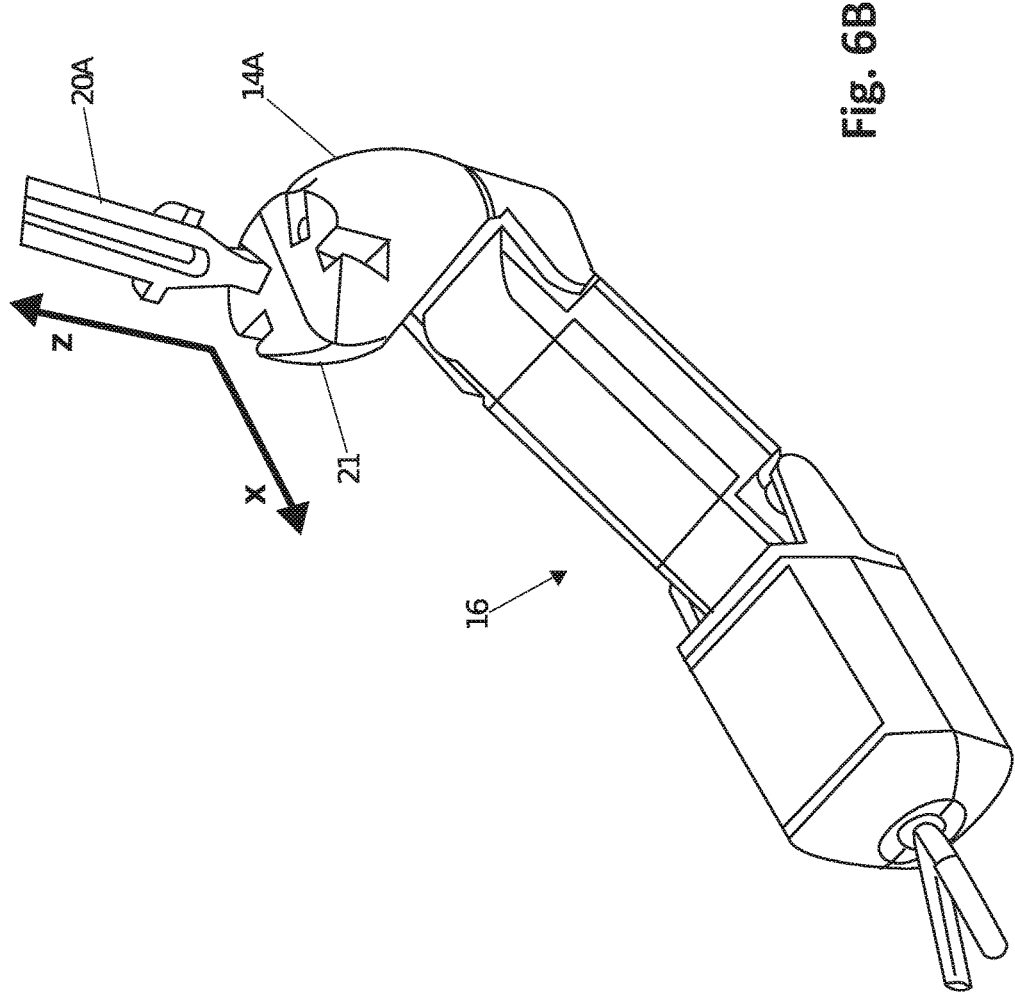

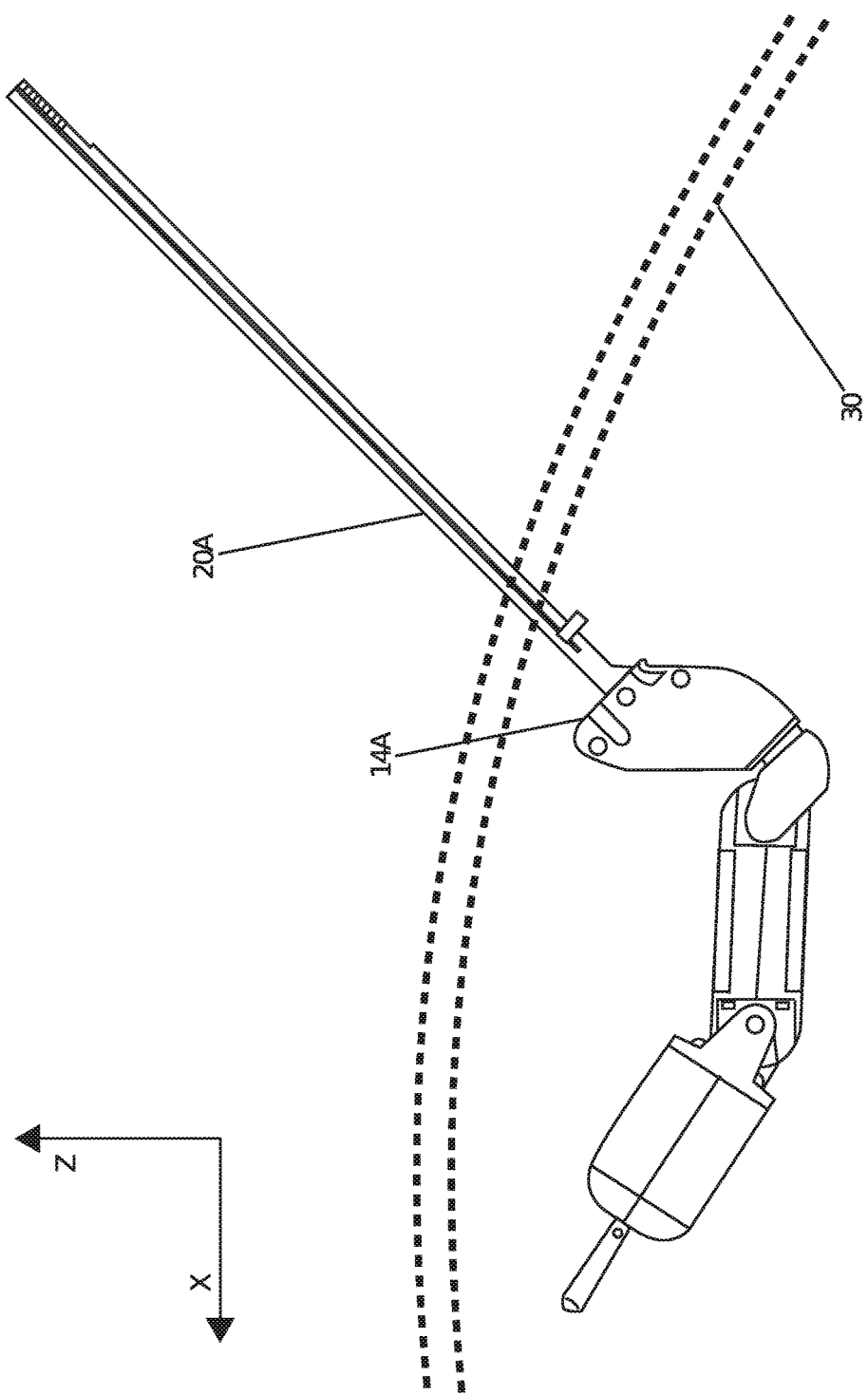

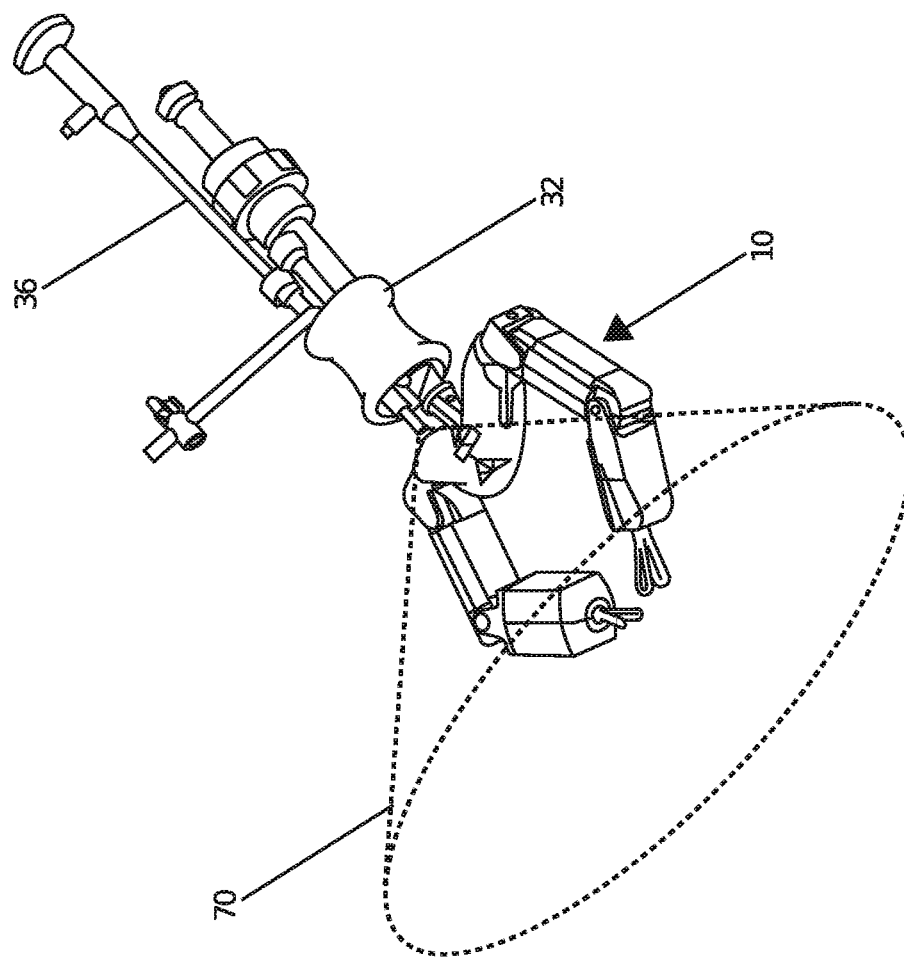

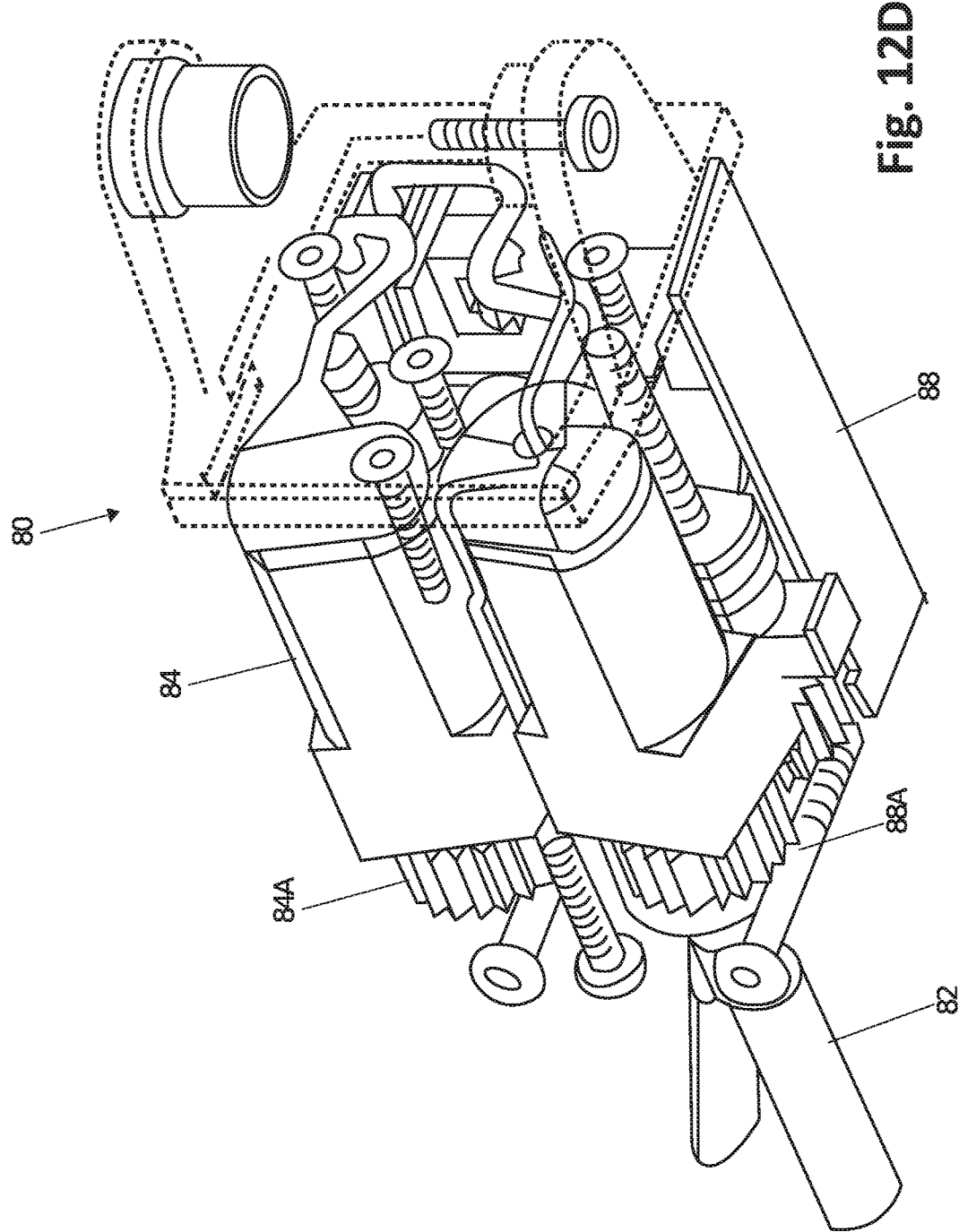

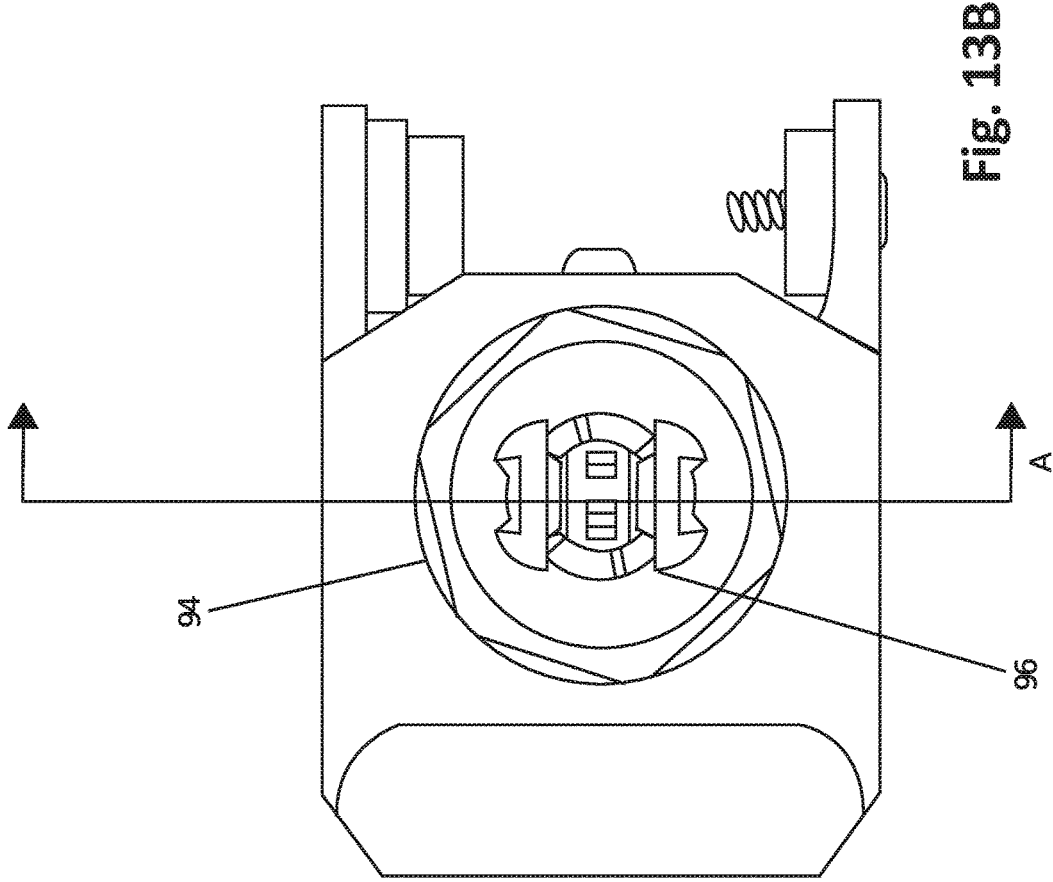

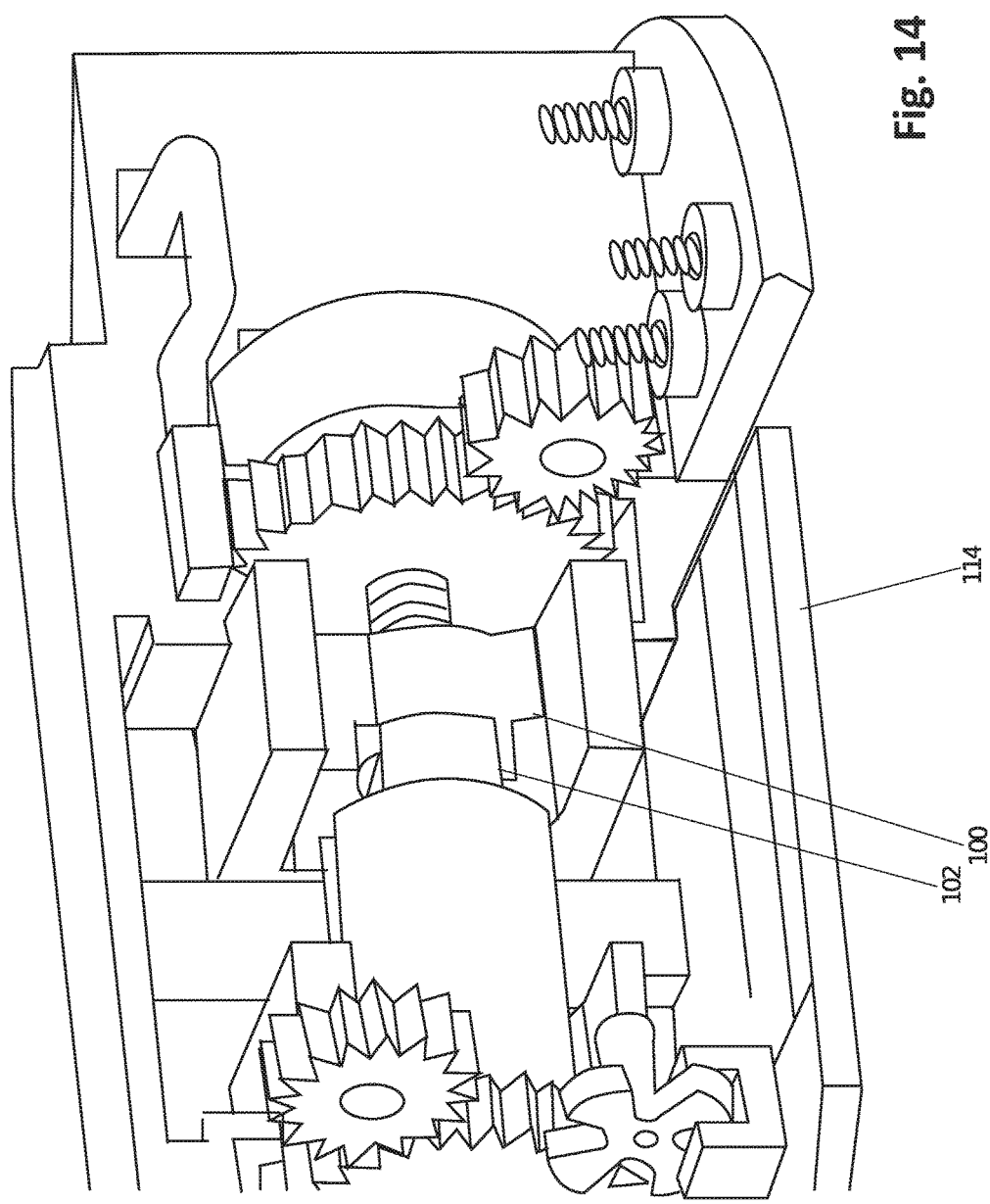

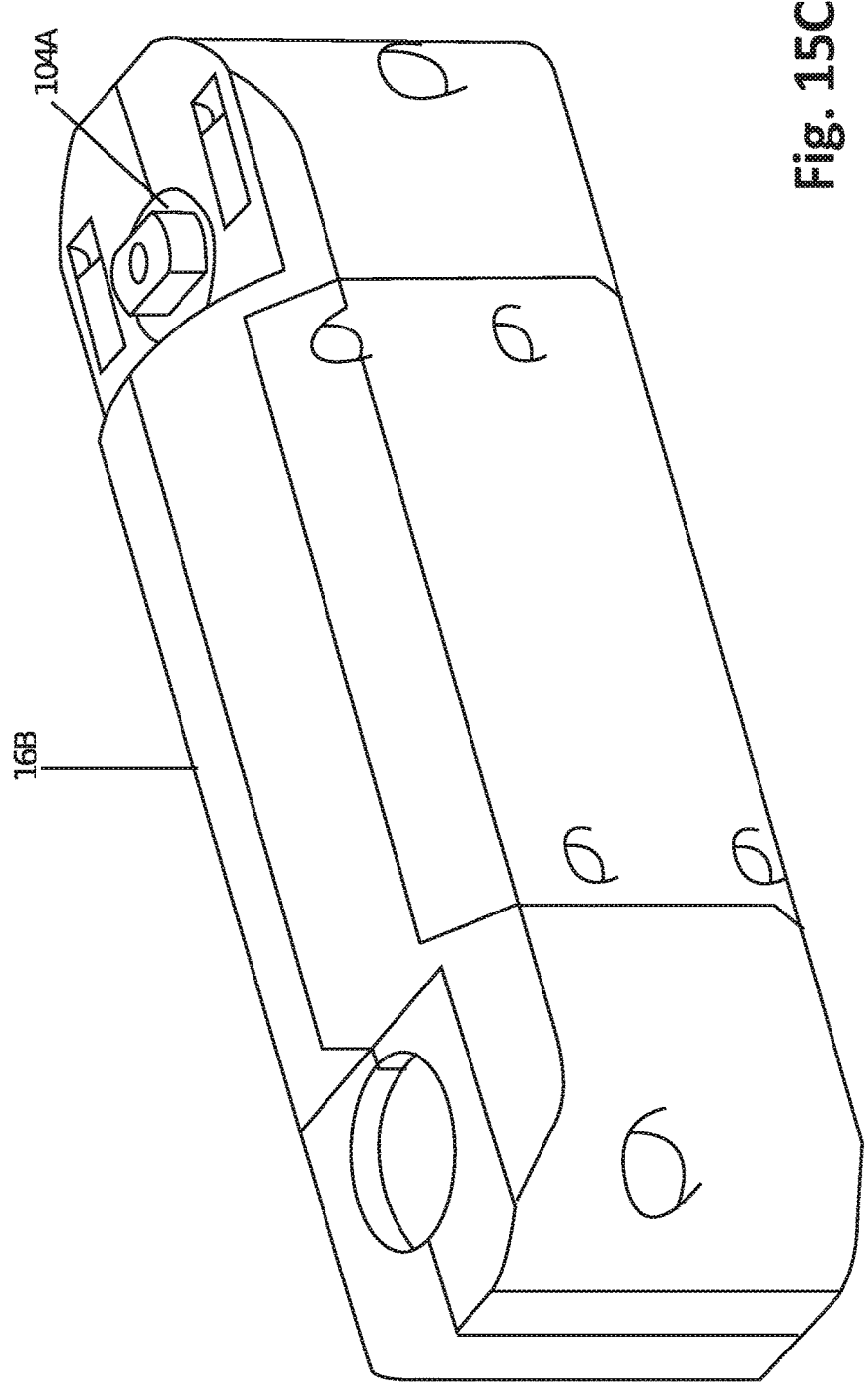

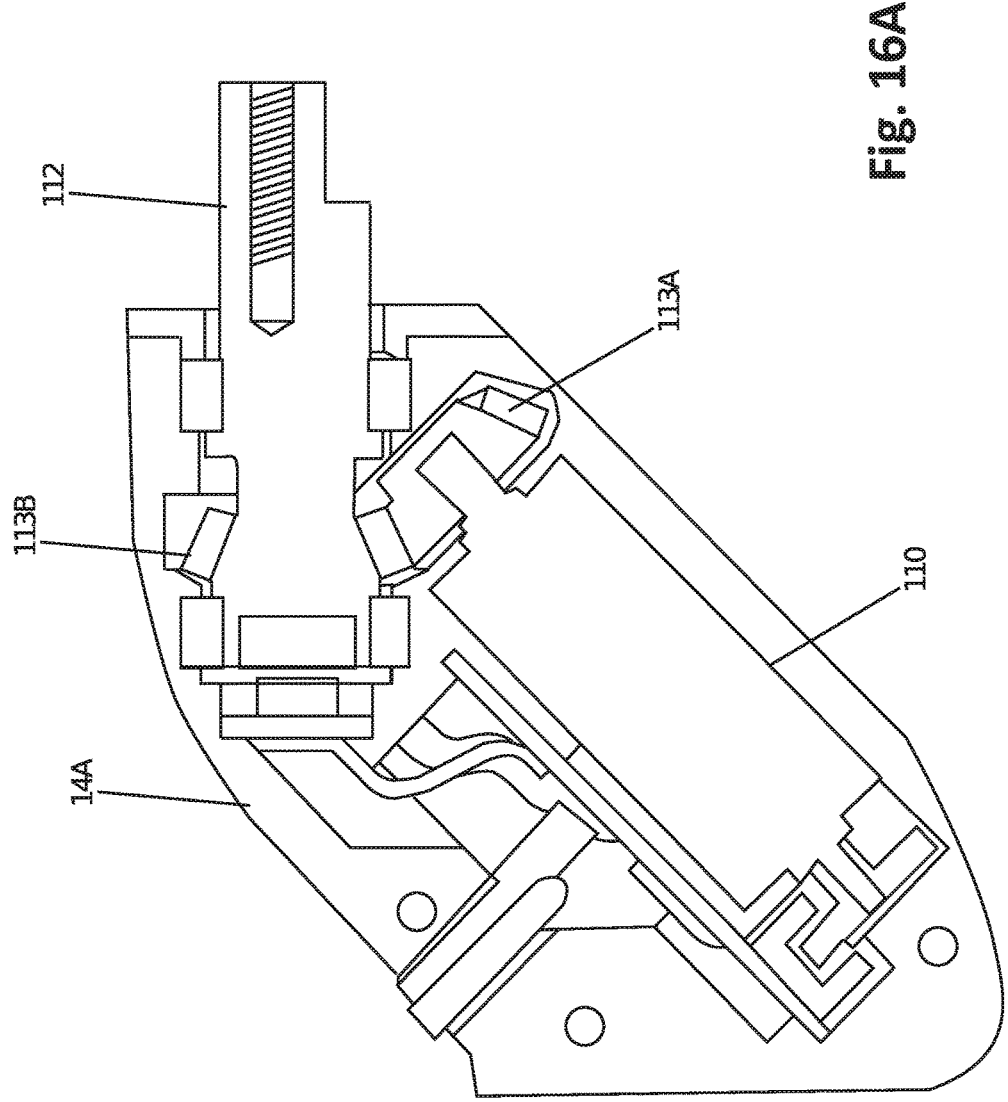

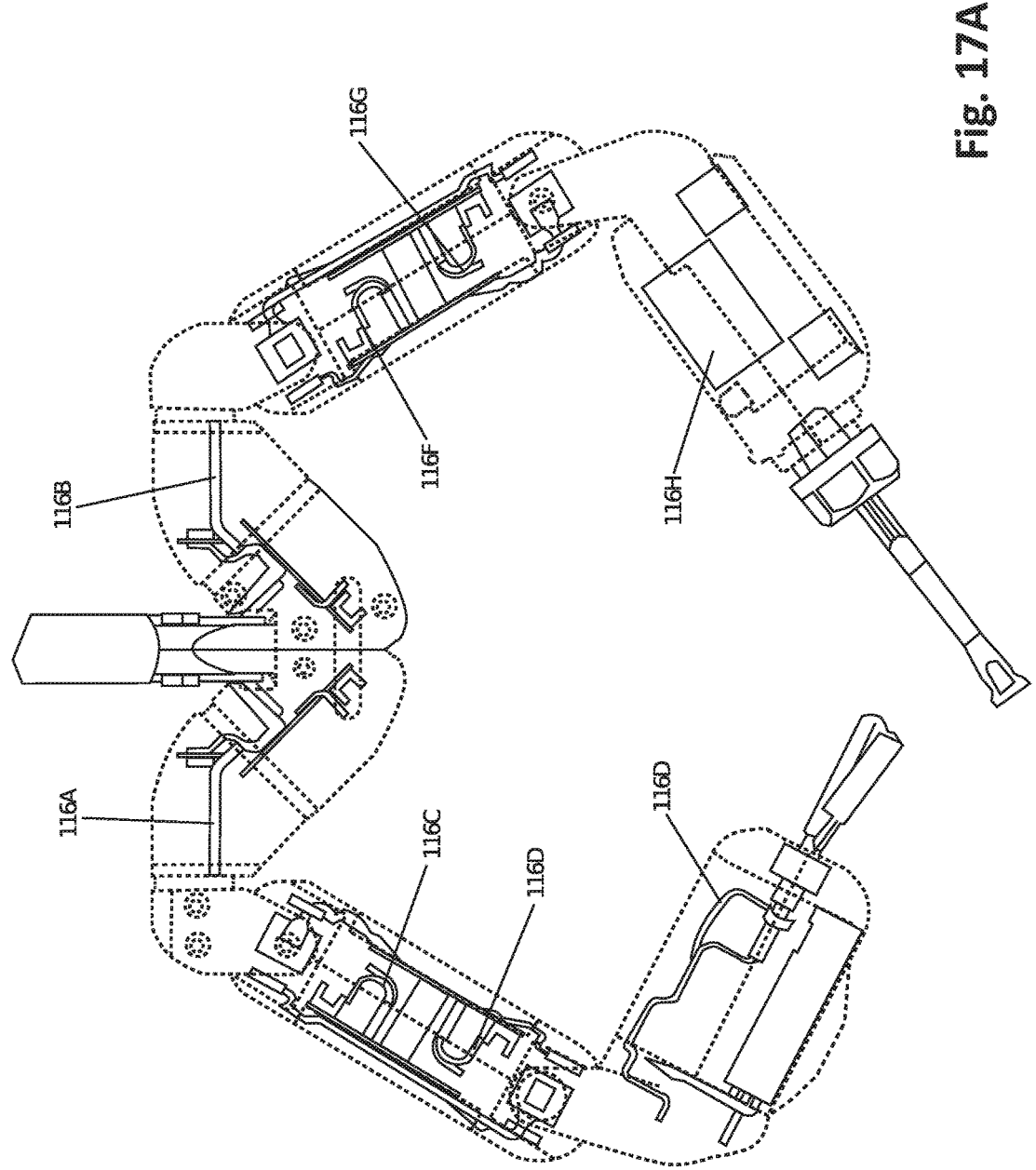

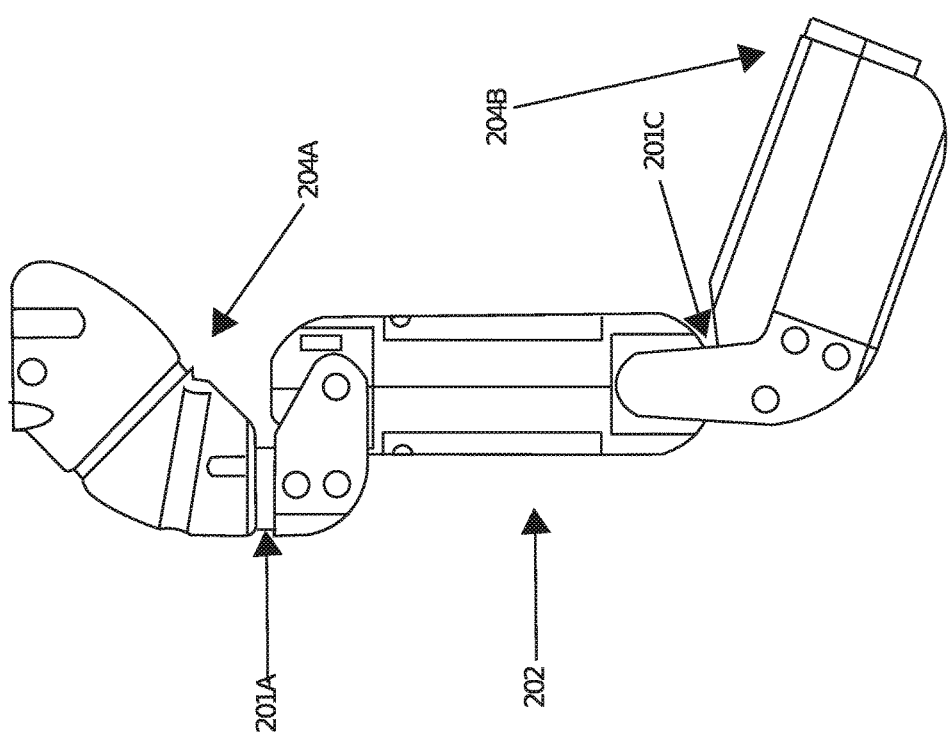

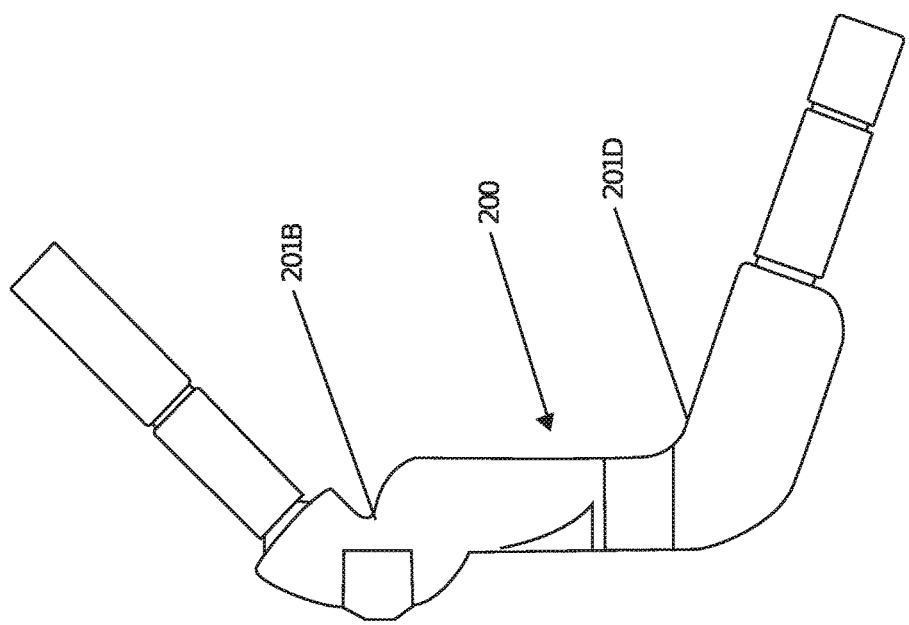

ROBOTIC DEVICES WITH ON BOARD CONTROL AND RELATED SYSTEMS AND DEVICES

CROSS REFERENCE TO RELATED APPLICATIONS

This application is a continuation of U.S. application Ser. No. 13/573,849, entitled "ROBOTIC SURGICAL DEVICES, SYSTEMS, AND RELATED METHODS," filed on Oct. 9, 2012, which claims priority to U.S. Provisional Application 61/680,809, filed Aug. 8, 2012, which is incorporated herein in its entirety by this reference.

GOVERNMENT SUPPORT

This invention was made with government support under Grant No. W81XWH-08-02-0043 awarded by the U.S. Army Medical Research and Materiel Command within the Department of Defense. Accordingly, the government has certain rights in this invention.

TECHNICAL FIELD

The embodiments disclosed herein relate to various medical devices and related components, including robotic and/or in vivo medical devices and related components. Certain embodiments include various robotic medical devices, including robotic devices that are disposed within a body cavity and positioned using a support component disposed through an orifice or opening in the body cavity. Further embodiment relate to methods of operating the above devices.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

BRIEF SUMMARY

Discussed herein are various robotic surgical devices and systems that can be disposed at least partially within a cavity of a patient and can be used for a variety of surgical procedures and tasks including, but not limited to, tissue biopsy, tissue dissection, or tissue retraction.

In Example 1, a modular surgical robotic system comprises a modular robotic device sized to be positioned completely within a patient further comprising a body component further comprising a first shoulder component and a second shoulder component, a first movable segmented robotic arm comprising a housing with at least one motor disposed within the housing and operationally connected to the body component by way of the first shoulder component, a second movable segmented robotic arm comprising a housing with at least one motor disposed within the housing and operationally connected to the body component by way of the second shoulder component, a first operational component operationally connected to the first robotic arm, and a second operational component operationally connected to the second robotic arm. The system further comprises a port configured for traversing the body of a patient, a support rod for crossing the port from the interior to exterior of the patient and connecting to the first and second body components, and an operations system for control of the modular robotic device from outside the patient by way of the port and support rod, the operations system in electrical communication with the modular robotic device.

Example 2 relates to the modular surgical robotic system of Example 1, wherein the modular robotic device may be assembled within the body cavity of the patient.

Example 3 relates to the modular surgical robotic system of Example 2, wherein the support rod is further comprised of a first support rod segment and a second support rod segment.

Example 4 relates to the modular surgical robotic system of Example 3, wherein the first support rod component and second support rod component are rotationally coupled to the first shoulder component and second shoulder component, respectively.

Example 5 relates to the modular surgical robotic system of Example 4, wherein the support rod is substantially enclosed in an overtube.

Example 6 relates to the modular surgical robotic system of Example 1, wherein the body component is cylindrical.

Example 7 relates to the modular surgical robotic system of Example 1, wherein the first shoulder component and second shoulder component are set at an obtuse angle from one another.

Example 8 relates to the modular surgical robotic system of Example 1, wherein the first operational component is chosen from a group consisting of a grasping component, a cauterizing component, a suturing component, an imaging component, an operational arm component, a sensor component, and a lighting component.

Example 9 relates to the modular surgical robotic system of Example 1, wherein the second operational component is chosen from a group consisting of a grasping component, a cauterizing component, a suturing component, an imaging component, an operational arm component, a sensor component, and a lighting component.

Example 10 relates to the modular surgical robotic system of Example 1, further comprising one or more motors for operation, rotation or movement of at least one of the first shoulder, the second shoulder, the first segmented arm, the second segmented arm, the first operational component, and the second operational component.

Example 11 relates to the modular surgical robotic system of Example 1, wherein the port creates an insufflation seal in the body.

In Example 12, a modular surgical robotic system comprises a modular robotic device sized to be positioned completely within a patient. The device comprises a first shoulder component, a second shoulder component, a body component, formed by the connection of the first shoulder component to the second shoulder component, a first movable segmented robotic arm comprising at least one motor and operationally connected to the body component by way of the first shoulder component, a second movable segmented robotic arm comprising at least one motor and operationally connected to the body component by way of the second shoulder component, a first operational component operationally connected to the first robotic arm, and a second operational component operationally connected to the second robotic arm. The system further comprises a port configured for traversing the body of a patient and an operations system for control of the modular robotic device from outside the patient by way of the port and support rod, the operations system in electrical communication with the modular robotic device.

Example 13 relates to the modular surgical robotic system of Example 12, wherein the modular robotic device may be assembled within the body cavity of the patient.

Example 14 relates to the modular surgical robotic system of Example 12, wherein the body component is cylindrical.

Example 15 relates to the modular surgical robotic system of Example 12, wherein the first shoulder component and second shoulder component are set at an obtuse angle from one another.

Example 16 relates to the modular surgical robotic system of Example 12, wherein the first operational component is chosen from a group consisting of a grasping component, a cauterizing component, a suturing component, an imaging component, an operational arm component, a sensor component, and a lighting component.

Example 17 relates to the modular surgical robotic system of Example 12, wherein the second operational component is chosen from a group consisting of a grasping component, a cauterizing component, a suturing component, an imaging component, an operational arm component, a sensor component, and a lighting component.

Example 18 relates to the modular surgical robotic system of Example 12, further comprising one or more motors for operation, rotation or movement of at least one of the first shoulder, the second shoulder, the first segmented arm, the second segmented arm, the first operational component, and the second operational component.

Example 19 relates to the modular surgical robotic system of Example 12, wherein the port is constructed and arranged to create an insufflation seal in the body of the patient.

BRIEF DESCRIPTION OF THE DRAWINGS

FIG. 1B is a perspective view of the device of FIG. 1A.

FIG. 2A is a perspective view of a robotic medical device, according to one embodiment.

FIG. 3 is a perspective view of a robotic device and related equipment, according to one embodiment.

FIG. 5 is a perspective view of a robotic device and related equipment, according to one embodiment.

FIG. 6A is a perspective view of the arm of a robotic device poised to be inserted into a patient's cavity, according to one embodiment.

FIG. 6B is a perspective view of the arm of FIG. 6A, rotated to show an alternate angle.

FIG. 7 is a side view of a robotic device during insertion and assembly, according to one embodiment.

FIG. 11 is a view of a robotic device and related equipment, according to one embodiment.

FIG. 12D is a cutaway perspective view of a robotic medical device, according to one embodiment.

FIG. 13B is a front view of a forearm of a robotic medical device, according to one embodiment.

FIG. 14 shows a cut away view of a robotic forearm, according to one embodiment.

FIG. 15C shows a perspective view of a robotic upper arm, according to one embodiment.

FIG. 16A shows a cutaway side view of a robotic shoulder, according to one embodiment.

FIG. 17A shows a top cutaway view of robotic device cabling, according to one embodiment.

FIG. 20A shows a robotic arm according to one embodiment.

FIG. 20B shows a robotic arm sleeve mold, according to one embodiment.

DETAILED DESCRIPTION

Figure 1A:
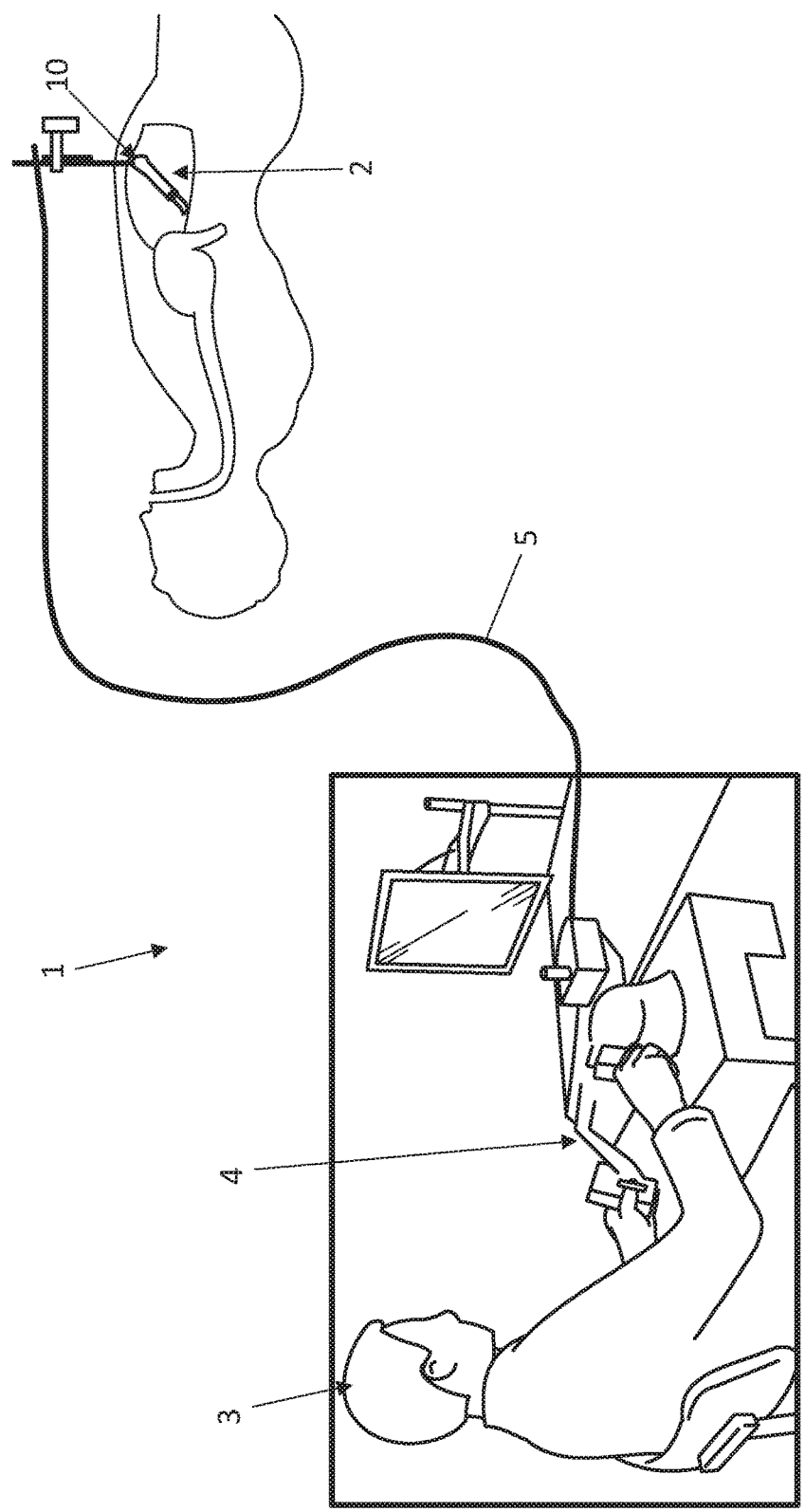
FIG. 1A is a diagram showing a robotic surgical system, including a robotic device positioned inside a body, according to one embodiment.

The various systems and devices disclosed herein relate to devices for use in medical procedures and systems. More specifically, various embodiments relate to various medical devices, including robotic devices and related methods and systems.

It is understood that the various embodiments of robotic devices and related methods and systems disclosed herein can be incorporated into or used with any other known medical devices, systems, and methods.

For example, the various embodiments disclosed herein may be incorporated into or used with any of the medical devices and systems disclosed in copending U.S. application Ser. No. 12/192,779 (filed on Aug. 15, 2008 and entitled "Modular and Cooperative Medical Devices and Related Systems and Methods"), U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), Ser. No. 11/947,097 (filed on Nov. 27, 2007 and entitled "Robotic Devices with Agent Delivery Components and Related Methods"), Ser. No. 11/932,516 (filed on Oct. 31, 2007 and entitled "Robot for Surgical Applications"), Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), Ser. No. 12/171,413 (filed on Jul. 11, 2008 and entitled "Methods and Systems of Actuation in Robotic Devices"), 60/956,032 (filed on Aug. 15, 2007), 60/983,445 (filed on Oct. 29, 2007), 60/990,062 (filed on Nov. 26, 2007), 60/990,076 (filed on Nov. 26, 2007), 60/990,086 (filed on Nov. 26, 2007), 60/990,106 (filed on Nov. 26, 2007), 60/990,470 (filed on Nov. 27, 2007), 61/025,346 (filed on Feb. 1, 2008), 61/030,588 (filed on Feb. 22, 2008), 61/030,617 (filed on Feb. 22, 2008), U.S. Pat. No. 8,179,073 (issued May 15, 2011, and entitled "Robotic Devices with Agent Delivery Components and Related Methods"), Ser. No. 12/324,364 (filed Nov. 26, 2008, U.S. Published App. 2009/0171373 and entitled "Multifunctional Operational Component for Robotic Devices"), and Ser. No. 13/493,725 (filed Jun. 11, 2012 and entitled "Methods, Systems, and Devices Relating to Surgical End Effectors"), all of which are hereby incorporated herein by reference in their entireties.

Certain device and system implementations disclosed in the applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

FIGS. 1A and 1B depict an exemplary system 1 that includes a robotic surgical device 10 disposed within the inflated peritoneal cavity 2 of a patient. It is understood that the various device and system embodiments disclosed herein, including the system 1 of FIGS. 1A and 1B, can be used for a variety of surgical procedures and tasks including, but not limited to, tissue biopsy, tissue dissection, or tissue retraction. For example, as shown in FIGS. 1A and 1B in accordance with one embodiment, the device 10 can be used to dissect tissue in the peritoneal cavity 2. In this system embodiment, a user (such as, for example, a surgeon) 3 operates a user interface 4 to control the device 10. The interface 4 is operably coupled to the device 10 by a cable 5 or other type of physical connection that provides for electronic power and/or electrical communication back and forth between the interface 4 and the device 10. Alternatively, the interface 4 can be operably coupled to the device 10 wirelessly. It is understood that the device embodiments disclosed herein can also be used with any other known system, including any of the systems disclosed in the various patent applications incorporated by reference above and elsewhere herein.

FIG. 2A depicts a robotic medical device 10, in accordance with one implementation. According to one embodiment, the device is an in vivo device. This device 10 embodiment as shown includes a body 12 that has two components 14A, 14B, which in this embodiment are cylindrical components 14A, 14B at an approximately 120 degree angle to each other. The cylindrical components 14A, 14B can also be referred to herein as shoulders, including a right shoulder 14A and a left shoulder 14B. In the embodiment depicted in FIG. 2A, the two components 14A, 14B are coupled directly to each other. Alternatively, the two components are not coupled to each other or, in another option, can be individually coupled to an access port used in the surgery. In a further alternative, the body 12 (and any body of any device embodiment disclosed herein) can be a single component and further can be any of the device body embodiments disclosed in the various patent applications incorporated by reference above and elsewhere herein.

Figure 8:
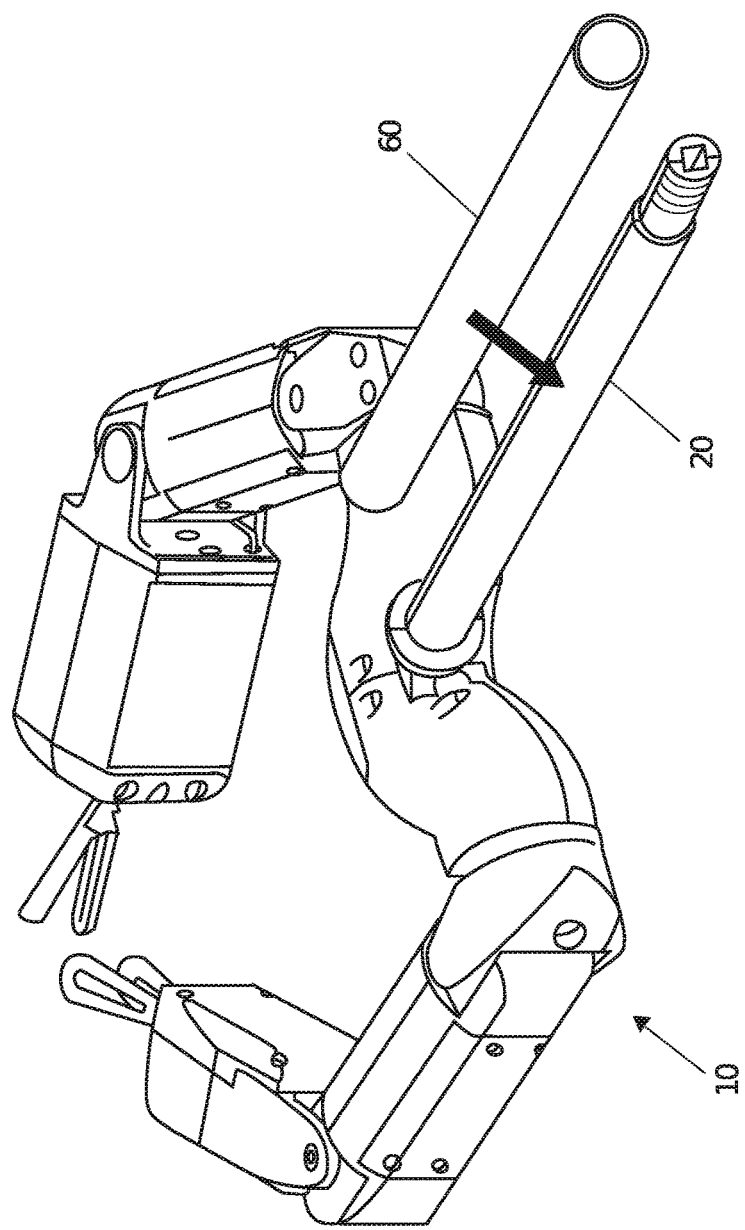
FIG. 8 is another perspective view of the robotic device with an overtube for assembly, according to one embodiment.

The body 12 is connected to two arms 16, 18 in one example of the device. In the implementation shown, the right shoulder 14A is coupled to right arm 16 and left shoulder 14B is coupled to left arm 18. In addition, the body 12 is also coupled to a support component 20, as best shown in FIG. 8. In accordance with one implementation as shown in FIGS. 6A and 6B and described in additional detail below, the support rod 20 as configured is a support rod 20 that is made of two coupleable support rod components 20A, 20B, each of which is independently attached to one of the body components 14A, 14B. More specifically, the support component 20 has a first support rod component 20A that is coupled to the first shoulder 14A and a second support rod component 20B that is coupled to the second shoulder component 14B. Alternatively, the support component 20 can be a single, integral component coupled to the body 12. In certain implementations, the support component 20 can be a rod, tube, or other applicable shape.

Returning to FIG. 2A, each of the arms 16, 18 have a first joint 16A, 18A (each of which can also be referred to as a "shoulder joint") that is coupled to the body components 14A, 14B. Each first joint 16A, 18A is coupled to a first link 16B, 18B (also referred to as a "first segment," an "upper segment," or an "upper arm"), each of which is rotatably coupled to a second link 16C, 18C (also referred to as a "second segment," a "lower segment," or a "forearm") via a second joint 16D, 18D (each of which can also be referred to as an "elbow joint"). In addition, each arm 16, 18 also has an operational component (also referred to as an "end effector") 16E, 18E coupled to the forearm 16C, 18C. It is understood that the operational components 16E, 18E (and any of the operational components on any of the embodiments disclosed herein) can be any known operational components, including any of the operational components disclosed in the various patent applications incorporated by reference above and elsewhere herein. By way of example, the components 16E, 18E can be cautery devices, suturing devices, grasping devices, imaging devices, operational arm devices, sensor devices, lighting devices or any other known types of devices or components for use in surgical procedures.

As mentioned above and as shown in FIG. 2B, the first links 16B, 18B are coupled to the body 12 via shoulder joints 16A, 18A. In one embodiment, each shoulder joint 16A, 16B is a joint having two axes of rotation. For example, as will be described in further detail below, the left shoulder joint 18A can be configured to result in rotation of the upper arm 18B as shown by arrow A around axis AA (that substantially corresponds to the longitudinal axis of the body 12) and also as shown by arrow B around axis BB, which is substantially perpendicular to axis AA. Because right shoulder joint 16A and right upper arm 16B are substantially the same as the left shoulder joint 18A and the left upper arm 18B, the above description also applies to those substantially similar (or identical) components. Alternatively, any known joint can be used to couple the upper arms 16B, 18B to the body 12.

Figure 2B:
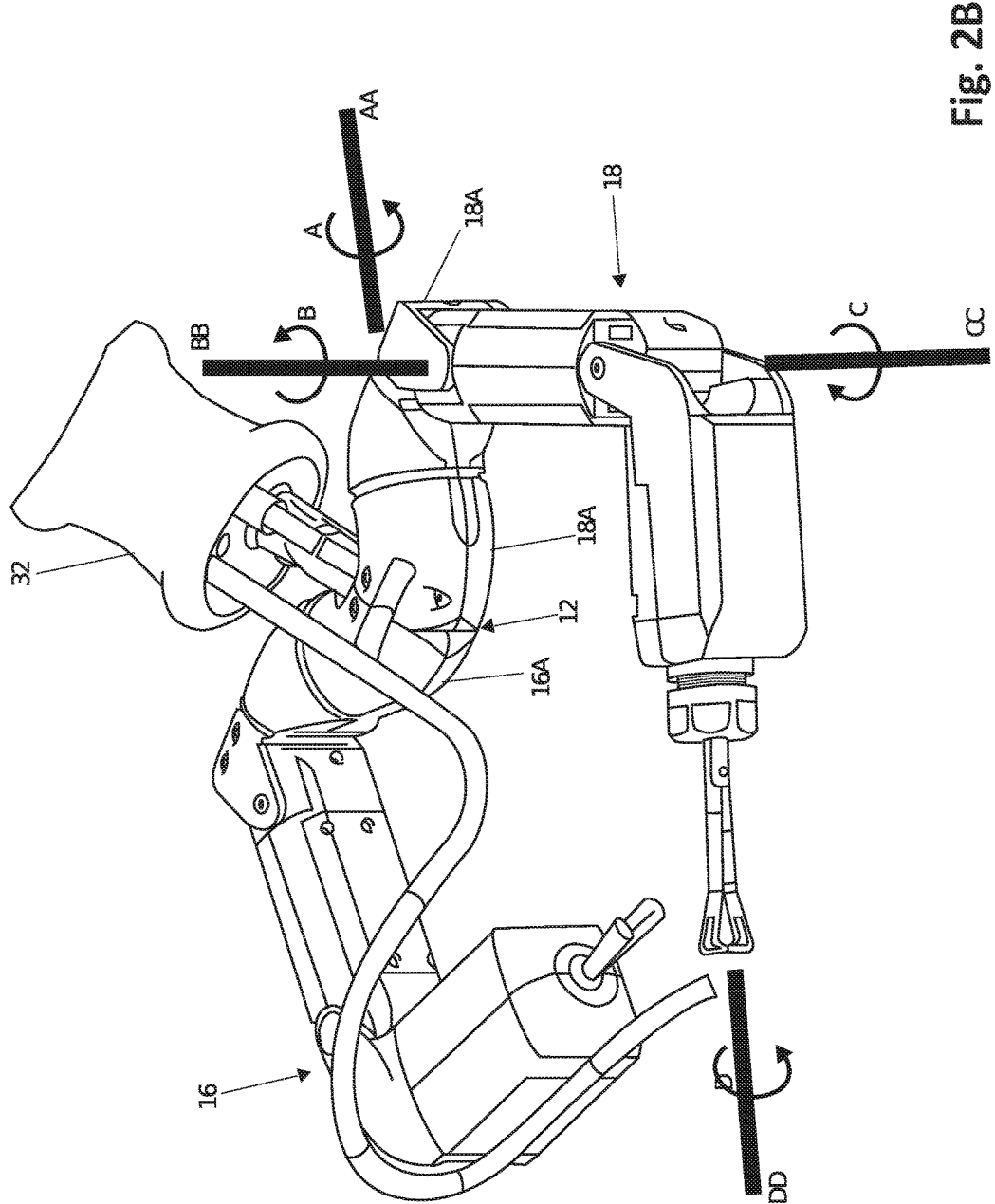
FIG. 2B is a perspective view of a robotic medical device showing the axes of rotation, according to one embodiment.

Continuing with FIG. 2B, the upper arms 16B, 18B, according to one implementation, are coupled to the forearms 16C, 18C, respectively, at the elbow joints 16D, 16D such that each of the forearms 16C, 18C can rotate. For example, the forearms 16C, 18C can rotate as shown by arrow C around axis CC. Further, the end effectors 16E, 18E can also rotate relative to the forearms 16C, 18C, respectively, as shown by arrow D around axis DD. In addition, each of the operational components 16E, 18E can also be actuated to move between at least two configurations, such as an open configuration and a closed configuration. Alternatively, the operational components 16E, 18E can be coupled to the forearms 16C, 18C, respectively, such that the operational components 16E, 18E can be moved or actuated in any known fashion.

According to one embodiment, the operational components 16E, 18E, such as graspers or scissors, are also removable from the forearms 16C, 18C, such that the operational components 16E, 18E are interchangeable with other operational components configured to perform other/different types of procedures. Returning to FIG. 2A, one operational component 16E is a grasper 16E commonly known as a babcock grasper and the other 18E is a vessel sealing grasper 18E. Alternatively, either or both of the components 16E, 18E can be cautery devices, suturing devices, grasping devices, or any other known types of devices or components for use in surgical procedures, or can be easily replaced with such components.

It is understood that the device 10 in this embodiment contains the motors (also referred to as "actuators," and intended to include any known source of motive force) that provide the motive force required to move the arms 16, 18 and the operational components 16E, 18E. In other words, the motors are contained within the device 10 itself (either in the body, the upper arms, the forearms or any and all of these), rather than being located outside the patient's body. Various motors incorporated into various device embodiments will be described in further detail below.

In use, as in the example shown in FIG. 3, the device 10 is positioned inside a patient's body cavity 30. For example, in FIG. 3, the body cavity 30 is the peritoneal cavity 30.

According to one implementation, the device 10 can be sealed inside the insufflated abdominal cavity 30 using a port 32 designed for single incision laparoscopic surgery. Alternatively, the device 10 can be inserted via a natural orifice, or be used in conjunction with other established methods for surgery. The device 10 is supported inside the abdominal cavity using the support rod 20 discussed above. The laparoscopic port 32 can also be used for insertion of an insufflation tube 34, a laparoscope 36 or other visualization device that may or may not be coupled to the device assembly. As an example, a 5 mm laparoscope 36 is shown in FIG. 3.

Figure 4:
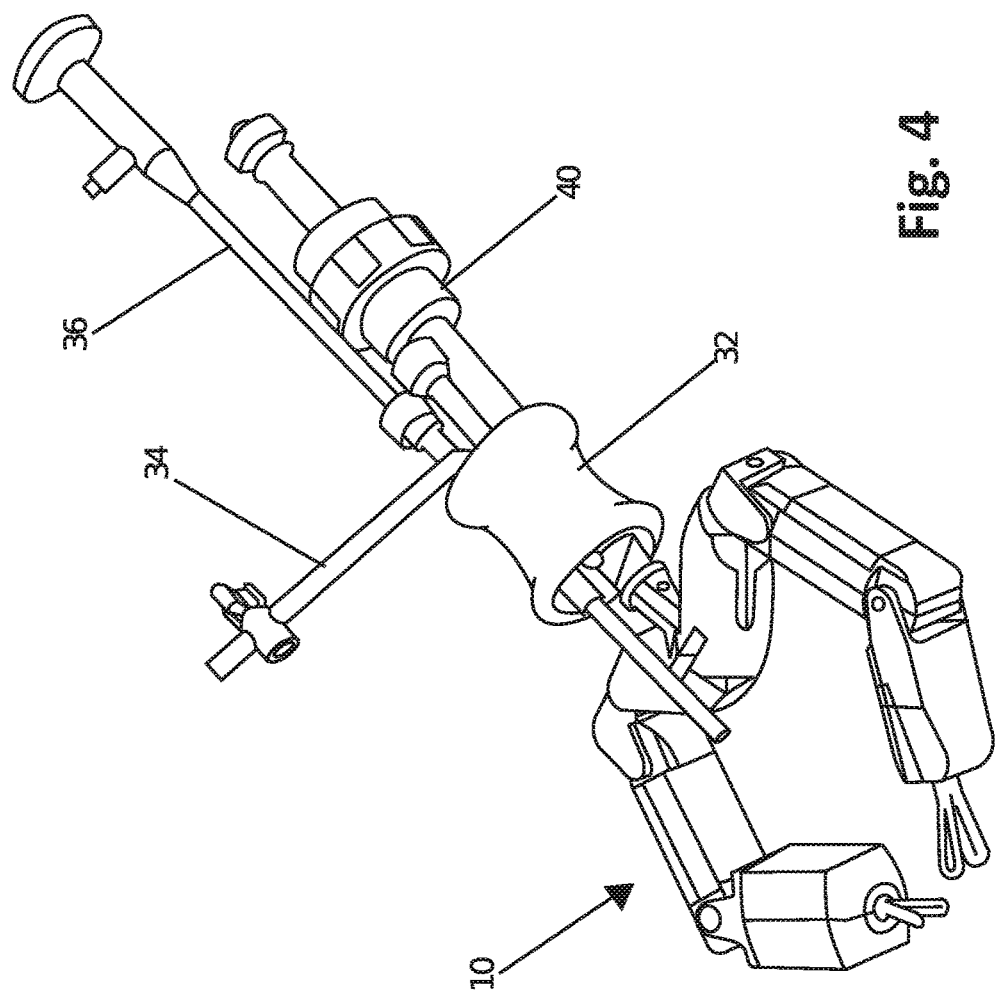
FIG. 4 is a perspective view of a robotic device and related equipment, according to one embodiment.

Alternatively, as shown in FIG. 4, a cannula or trocar 40 can be used in conjunction with the port device 32 to create a seal between the cavity and the external environment. Alternatively, any other known surgical instrument designed for such purposes can be used in conjunction with the port device 32 to create a seal between the cavity and the external environment, as is discussed below with regard to FIG. 9.

According to one alternative embodiment as shown in FIG. 5, a suction/irrigation tube 50 can be coupled with the device 10 and used for surgical suction and/or irrigation. In this embodiment, the tube 50 is coupled to the forearm 16C of the right arm 16. More specifically, the forearm 16C has a channel 52 defined on an exterior surface of the forearm 16C that is configured to receive and removably hold the tube 50. In use, the tube 50 can extend from the device 10 and through an orifice to an external device or system for use for surgical suction and/or irrigation. Alternatively, the tube 50 can be coupled to the left arm 18 or some other portion of the device 10. In a further alternative, the tube 50 can be disposed internally within the arm 16 or other component of the device 10.

In use, the device 10 can first be separated into the two smaller components as described above and then each of the two components are inserted in consecutive fashion through the orifice into the body cavity. In accordance with one implementation, due to the limitations associated with the amount of space in the cavity, each of the components can form a sequence of various configurations that make it possible to insert each such component into the cavity. That is, each component can be "stepped through" a sequence of configurations that allow the component to be inserted through the orifice and into the cavity.

For example, according to one implementation shown in FIGS. 6A and 6B, the device 10 can be inserted through a single orifice by physically separating the device 10 into separate, smaller components and inserting those components through the single orifice. In one example, the device can be separated into two "halves" or smaller components, in which one half 10A as shown in FIGS. 6A and 6B consists of the right shoulder 14A coupled to the right arm 16. Similarly, while not depicted in FIGS. 6A and 6B, the other half consists of the left shoulder 14B coupled to the left arm 18. It is understood that the left arm 18 is substantially similar to or the same as the right arm 16 such that the description of the right arm herein and the depiction in FIGS. 6A and 6B apply equally to the left arm 18 as well. In this implementation, the right shoulder 14A is coupled to the right support rod component 20A (and the left shoulder 14B is similarly coupled to the left support rod component 20B). Alternatively, this device 10 or any device contemplated herein can be separated into any two or more separable components.

FIGS. 6A and 6B show how the right support component 20A can be rotationally coupled to the shoulder 14A, thereby resulting in movement of the shoulder 14A in relation to the right support component 20A between at least two configurations, making insertion of the overall device into a patient's cavity easier. More specifically, the right device half 10A is shown in FIG. 6A in its operational configuration in relation to the right support component 20A such that the right device half 10A can be coupled to the left device half 10B (not shown) and thereby used to perform a procedure in the patient's cavity. Note the arrow 21 in FIG. 6A illustrating how the right support component 20A can rotate in relation to the right shoulder 14A. FIG. 6B, on the other hand, depicts the right device half 10A in its insertion configuration in which the right shoulder 14A has been rotated in relation to the right support component 20A, thereby making the device half 10A easier to insert through an orifice and into a patient's cavity. In use, the device half 10A is "stepped through" the two configurations to ease insertion. First, the device half 10A is placed in the insertion configuration of FIG. 6B and inserted through the orifice. Subsequently, once the right arm 16 is positioned inside the patient's cavity, the right shoulder 14A can be rotated in relation to the right support component 20A to move the device half 10A into the operational configuration of FIG. 6A such that the device half 10A can be coupled to the other half 10B and subsequently be used to perform a procedure.

When the device half 10A is properly positioned in the patient's cavity, the first support rod component 20A, which is coupled to the right shoulder 14A, is disposed through an orifice or any other kind of opening in the body cavity wall (shown as a dashed line in FIG. 7) such that the distal portion of the support rod component 20A coupled to the first shoulder 14A is disposed within the body cavity 30 while the proximal portion is disposed outside of the patient's body and can be attached to an external component (not shown) so as to provide stability or fixed positioning for the device.

Figure 9:
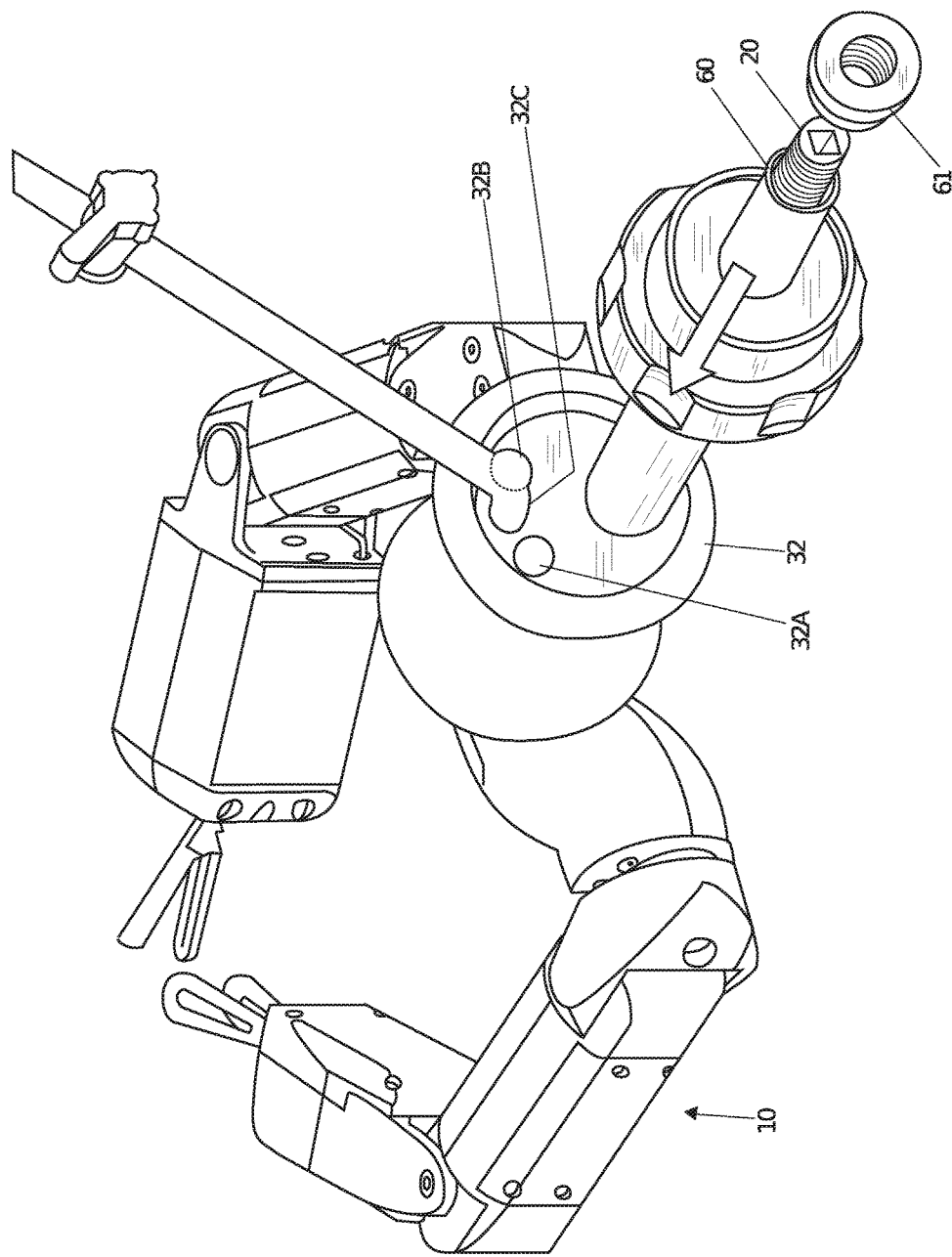
FIG. 9 is another perspective view of the robotic device during assembly, according to one embodiment.
Figure 10:
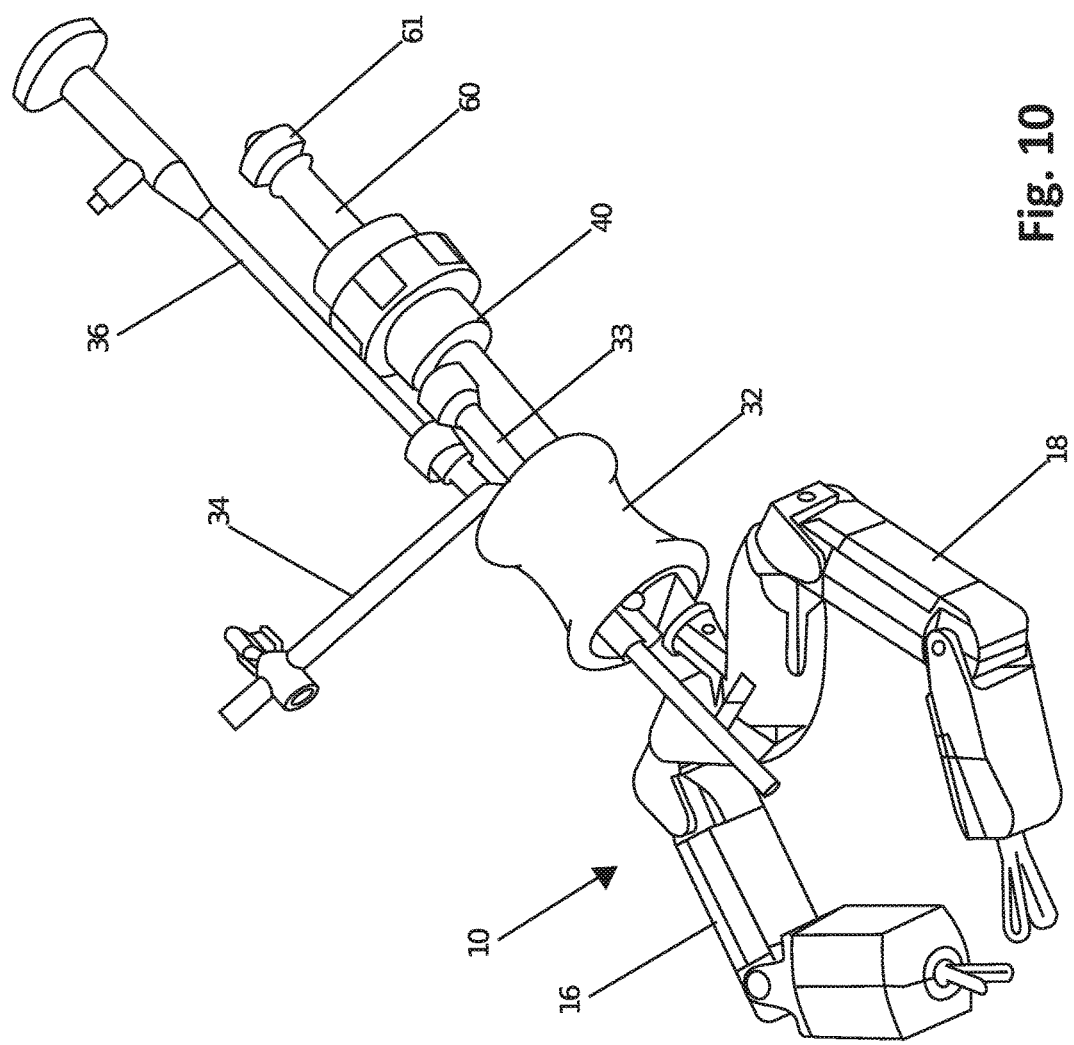
FIG. 10 is another perspective view of the robotic device and related equipment, according to one embodiment.

As discussed above, in this example, the two coupleable support rod components (such as 20A as shown in FIGS. 6A, 6B, and 7) can be positioned next to one another or coupled to each other form a cylindrical shape or a complete rod 20. In the example in FIG. 8, an overtube 60 can then be placed over the rod 20. As best shown in FIG. 9, this overtube 60 can be held in place with a threaded thumbscrew 61 and the entire rod 20 and overtube 60 assembly can then be inserted into the laparoscopic port 32. As best shown in FIG. 10, once assembled, other tools can then be inserted into the port such as a cannula for a suction/irrigation tube 34 as described above, a laparoscope 36 as described above, and/or other surgical instruments, and positioned through the port 32 via port openings 32A, 32B, 32C (as best shown in FIG. 9). These figures illustrate one example of how this assembly can be configured to accept a cannula for suction and irrigation or other component 33.

Alternatively, the device body 10 can be a single component that is coupled to both support rod components 20A, 20B, which are coupled to each other to form a full support rod 20.

Once assembled, an external device (not shown) can be used to stabilize the support component assembly. According to this implementation, the device 10 is maintained in a desired position or location within the body cavity of the patient using an external component that has a clamp that is removably attached to the support component 20. Alternatively, the external component can have any known attachment component that is capable of removably coupling to or attaching to support component.

As an example, the external component can be an iron intern (commercially available from Automated Medical Products Corp.) that includes several sections connected by joints that can be loosened and locked using knobs to allow the iron intern to be positioned in various orientations. The iron intern can be attached to rails on any standard surgical table or any other appropriate surface to provide support for device.

In use, according to one embodiment, the device 10 is positioned within the body cavity of the patient and the support component assembly 20 is positioned through a port 32 positioned in the hole or opening in the body cavity wall, as shown, for example, in FIG. 3. In one embodiment, the port 32 is a gel port through which the support component 20 can be disposed while still maintaining a fluidic seal that allows for the body cavity 30 of the patient to be inflated. Alternatively, any known port 32 that provides access for the support component 20 while maintaining a fluidic seal can be used. Also, any cables, electrical or otherwise, can be coupled to the device 10 via this port 32. In one embodiment, electrical cables pass through the support rod 20 or other support components.

FIG. 11 depicts one example of how a laparoscope 36 in one embodiment can be used in conjunction with the device 10 to provide visualization of the working space of the robotic assembly. More specifically, FIG. 11 shows how a "zero degree" laparoscope 36 can provide a large field of view (shown as cone 70) enabling the user to view the surgical environment. Other visualization means are also possible and these can either be separate from or attached to the robotic device 10. The visualization means can also enter though other orifices in the body cavity to be used independently or in conjunction with the robotic device 10.

FIGS. 12A-17 depict exemplary embodiments of how such a medical device can be mechanically and electrically constructed.

Figure 12A:
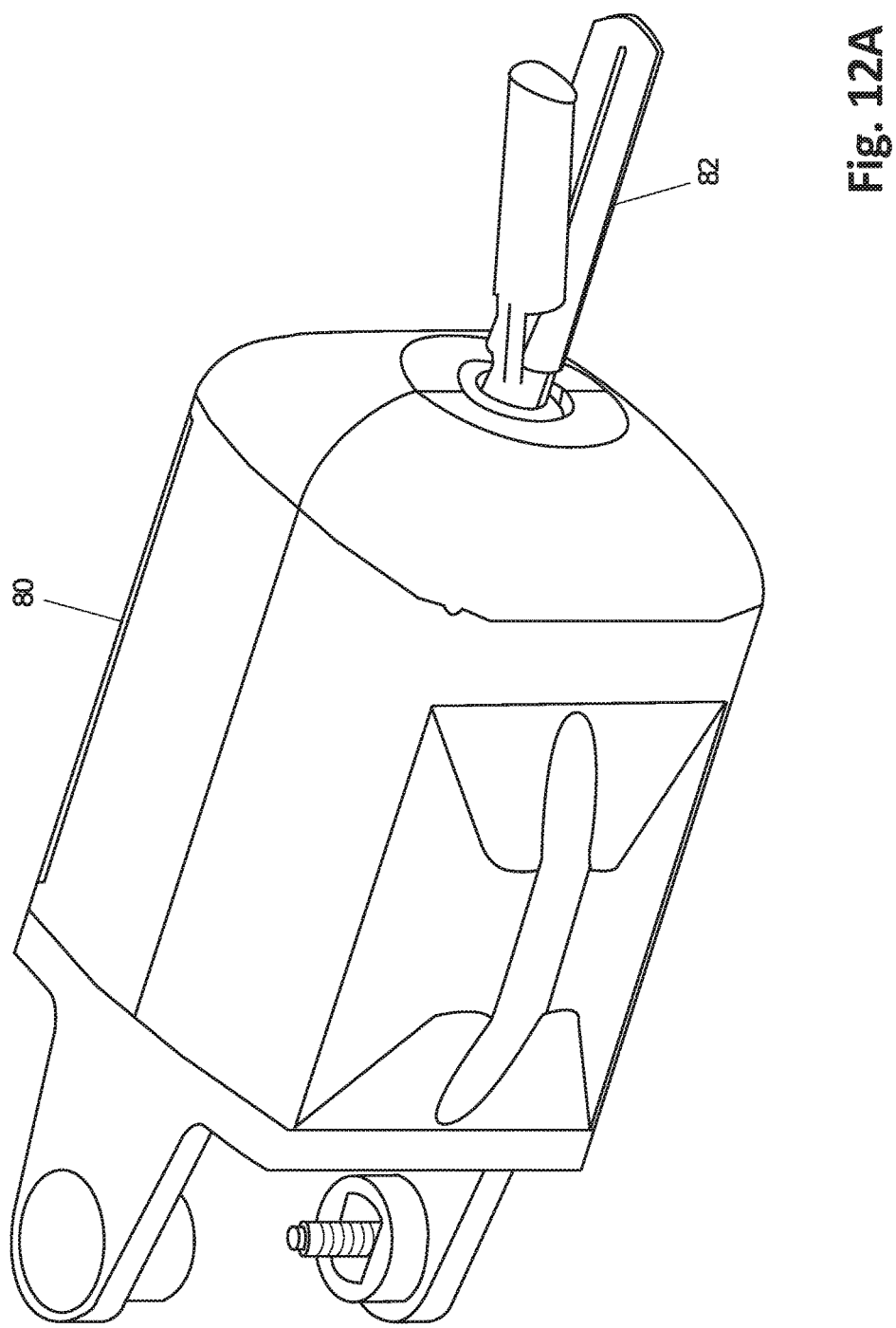
FIG. 12A is a perspective view of a robotic medical device, according to one embodiment.
Figure 12B:
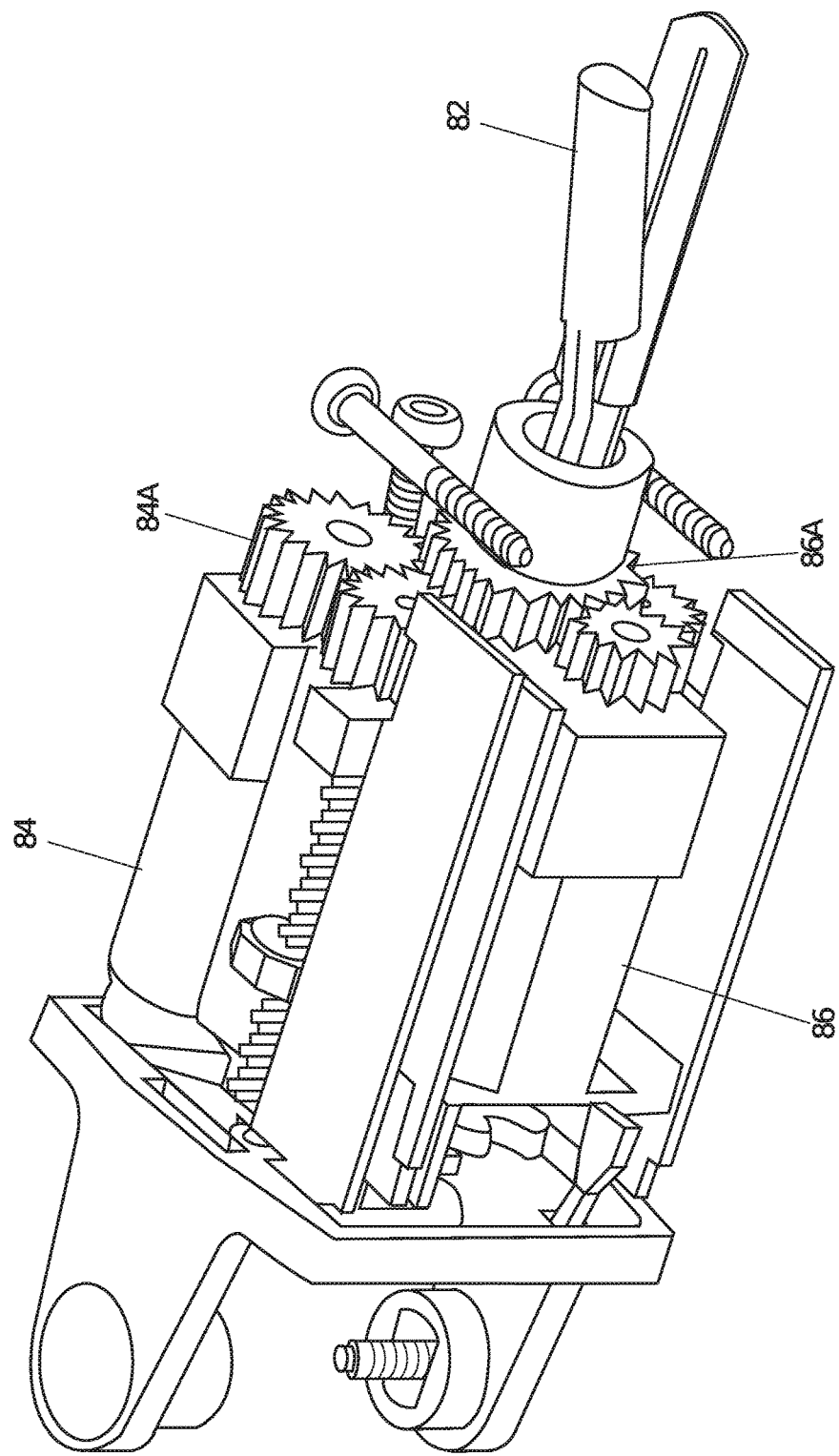
FIG. 12B is a cutaway perspective view of a robotic medical device, according to one embodiment.
Figure 12C:
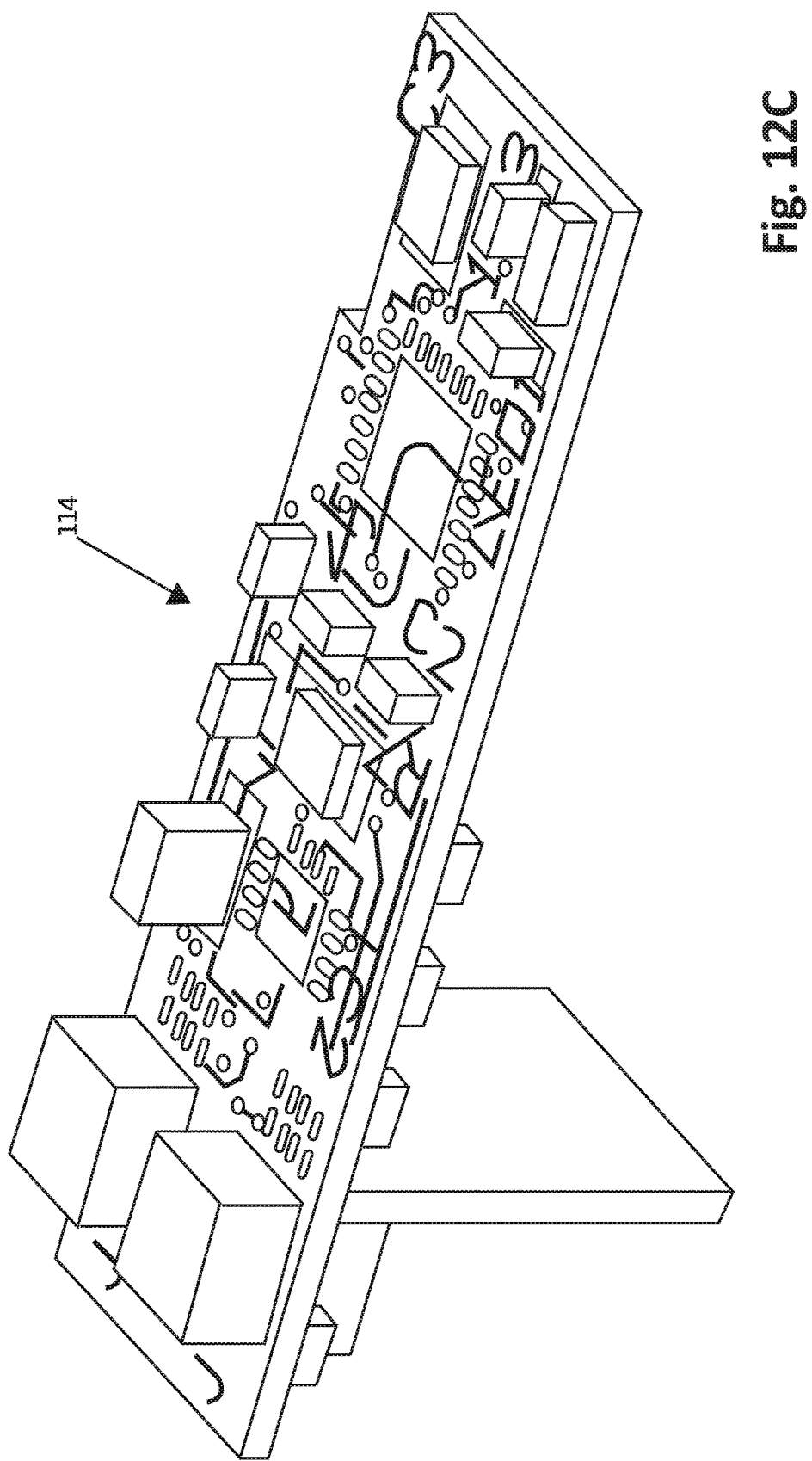
FIG. 12C is a perspective view of a printed circuit board of a robotic medical device, according to one embodiment.

FIGS. 12A-12D show one design of a forearm 80 having a vessel sealing operational component or end effector 82. The vessel sealing device 82 may or may not include a cutting component and different types of cautery techniques. In this example, as best shown in FIGS. 12B and 12D, a first actuator 84 is coupled to the end effector 82 by spur gears 84A, a second actuator 86 is coupled to the end effector 82 by spur gears 86A, and a third actuator 88 is coupled to the end effector by spur gears 88A. These first, second and third actuators 84, 86, 88 provide rotation of the end effector 82 along the axis of the forearm 80 (axis DD as described in FIG. 2), opening and closing motion for the end effector 82, and can cause a cutting device (not shown) to translate through the end effector 82.

FIGS. 12A-17 also show various printed circuit boards 114A-114J used to power and control the actuators. Each actuator has one or more sensors to measure the position of the components for control. These can include, but are not limited to, optical encoders, mechanical encoders, or potentiometers. Each sensor can either measure relative or absolute position.

Figure 13A:
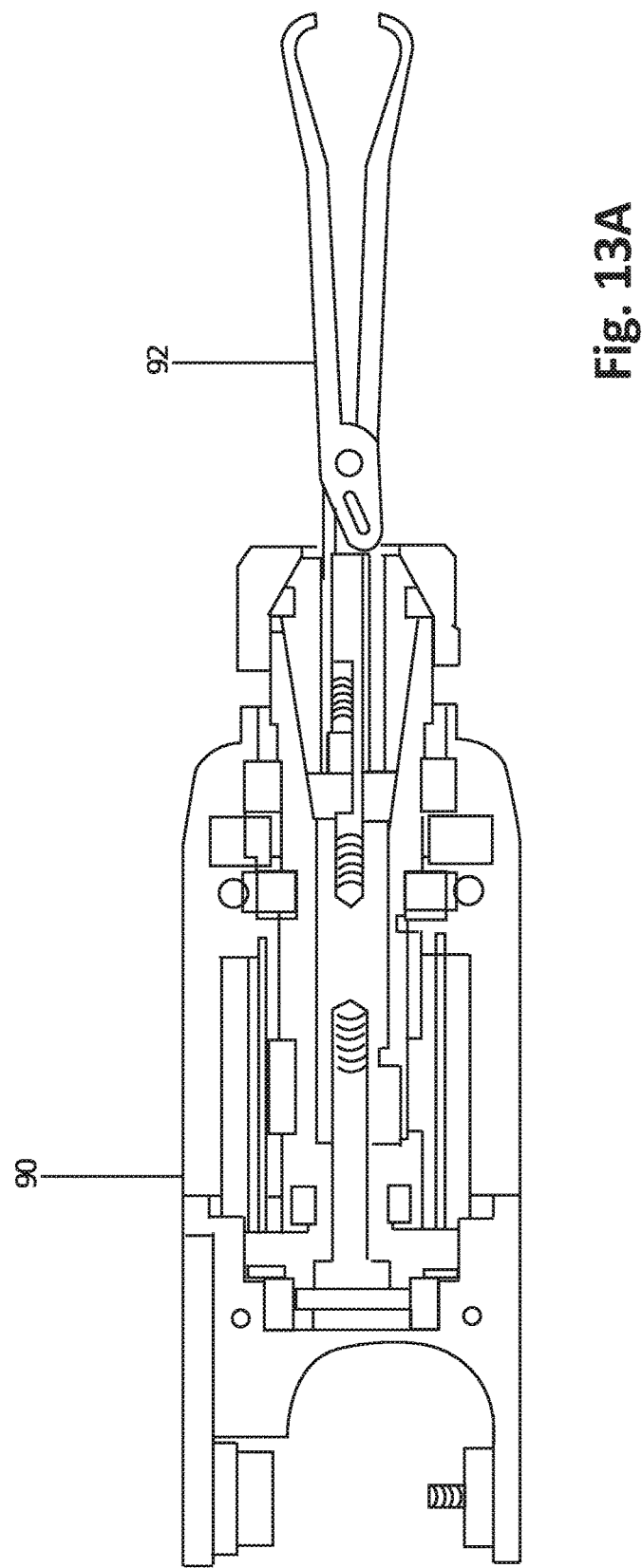
FIG. 13A is a side cutaway view of a robotic medical device, according to one embodiment.
Figure 13C:
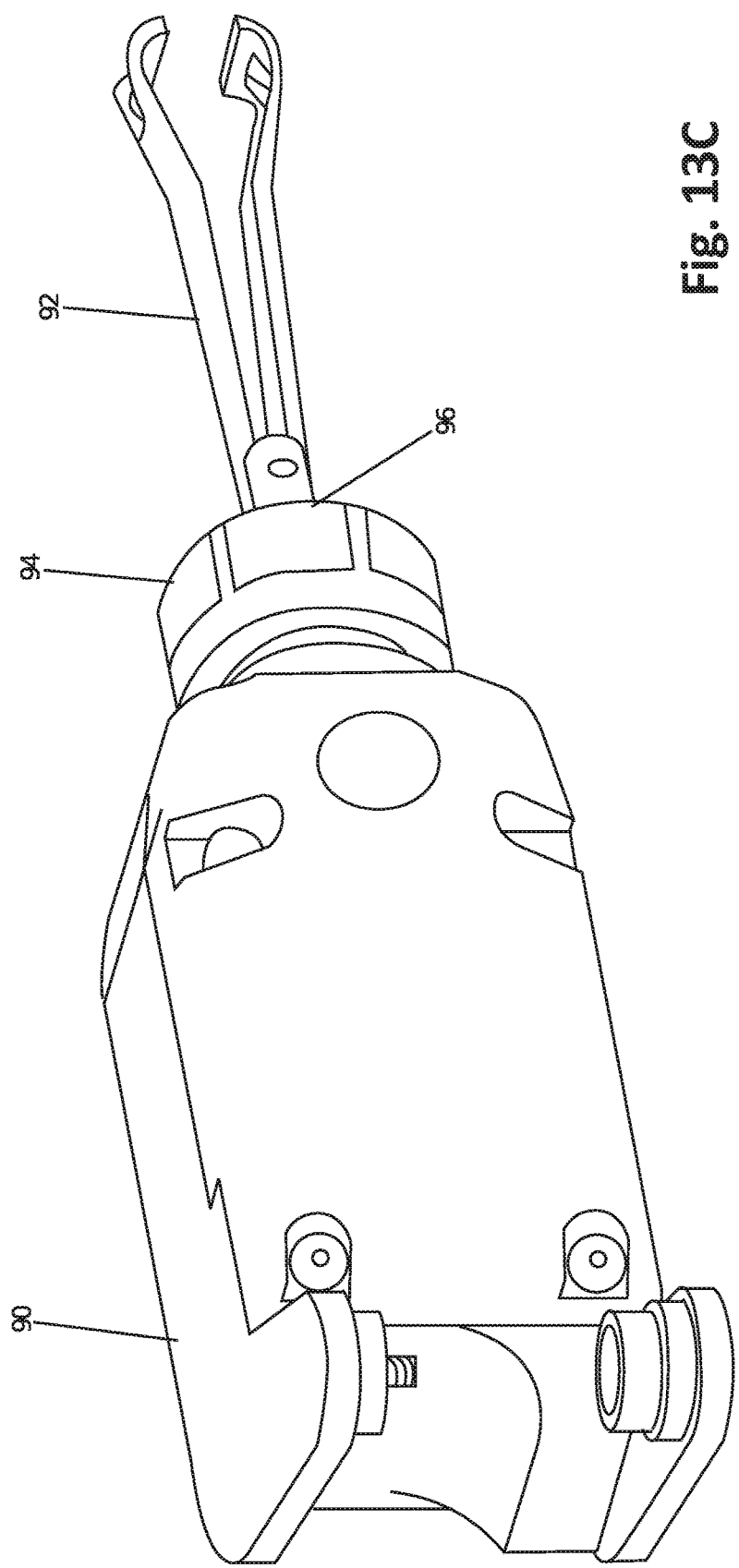
FIG. 13C is a rear perspective view of a forearm of a robotic medical device, according to one embodiment.
Figure 13D:
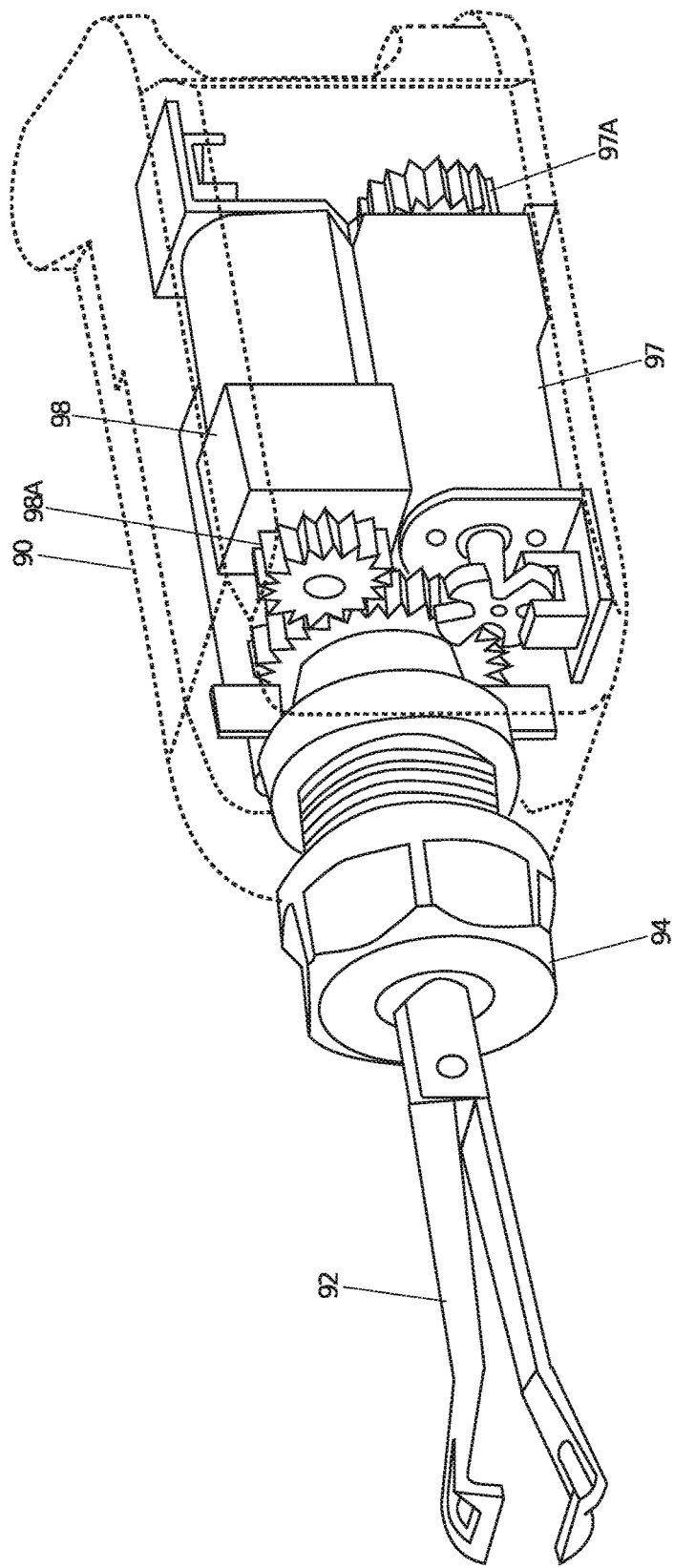
FIG. 13D is cutaway perspective view of a forearm of a robotic medical device, according to one embodiment.
Figure 15A:
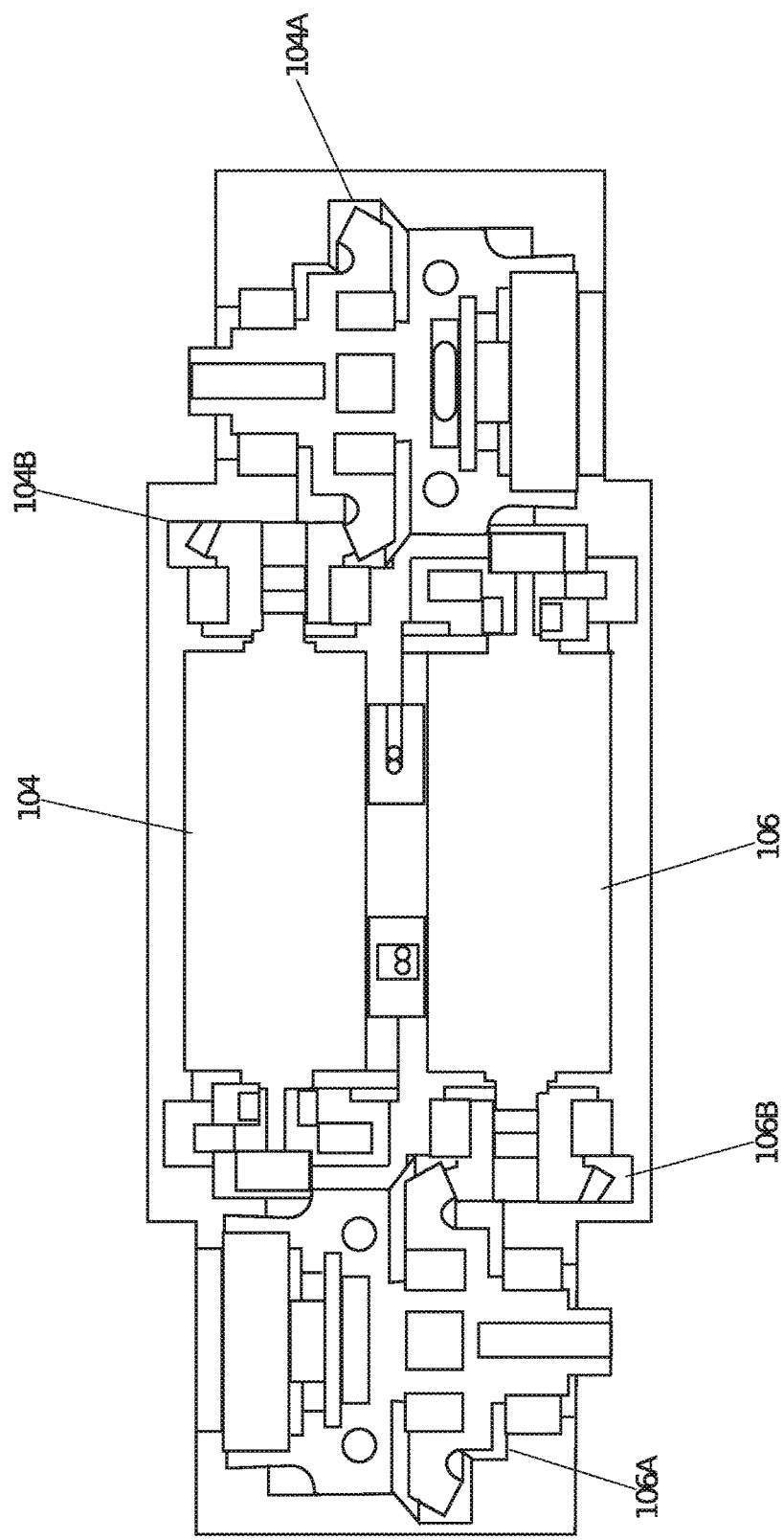
FIG. 15A shows a cutaway side view of a robotic upper arm, according to one embodiment.
Figure 15B:
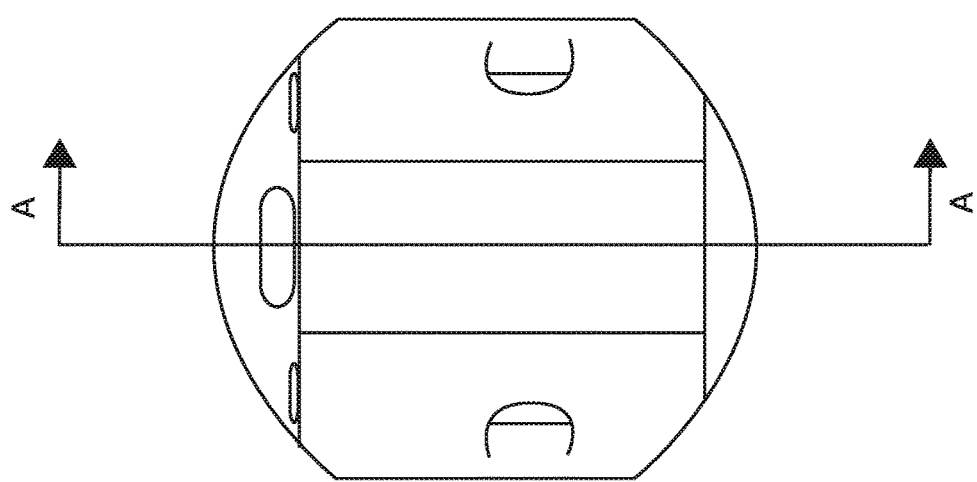
FIG. 15B shows an end view of a robotic upper arm, according to one embodiment.
Figure 15D:
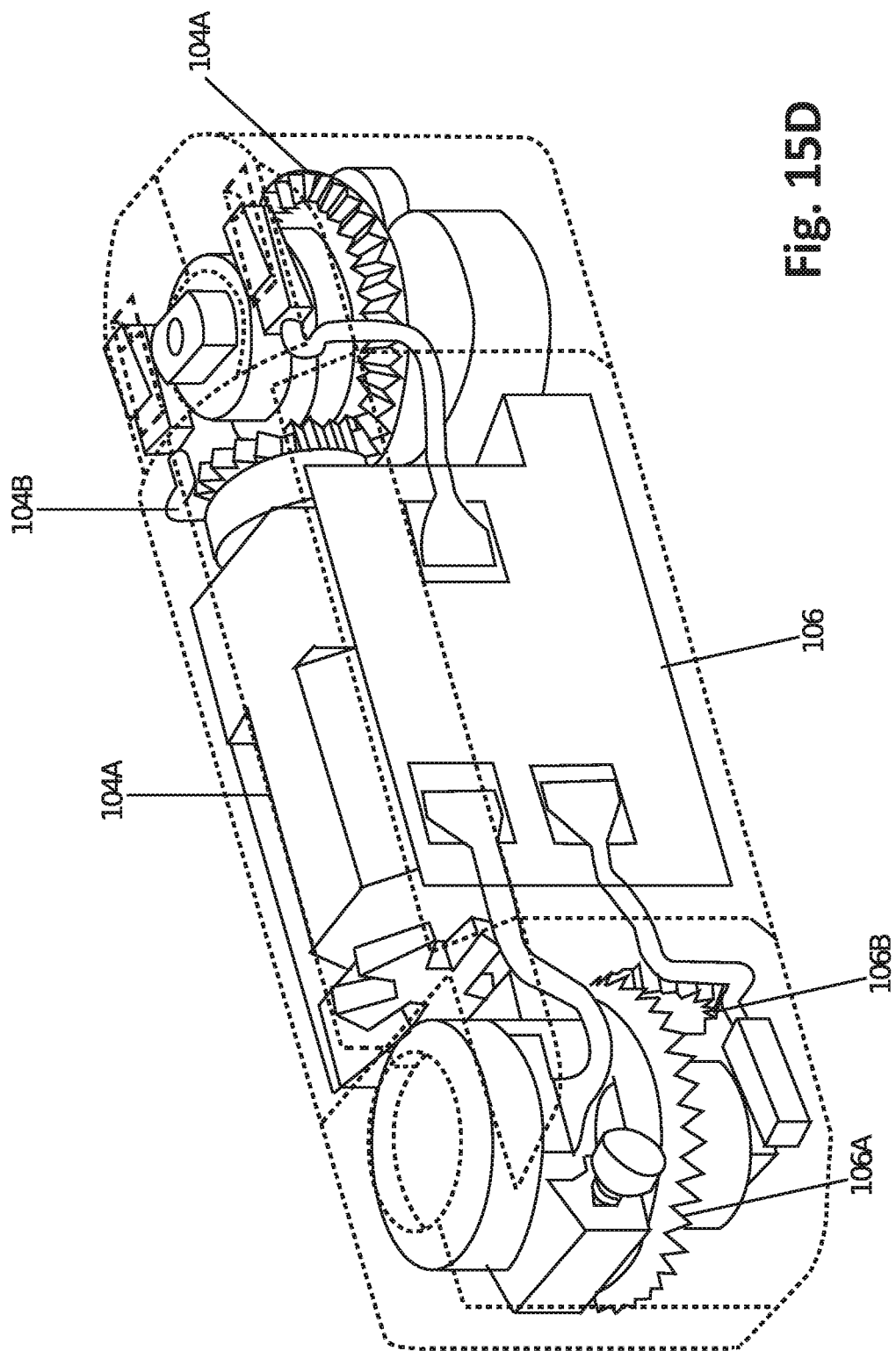
FIG. 15D shows a cutaway perspective view of a robotic upper arm, according to one embodiment.
Figure 16B:
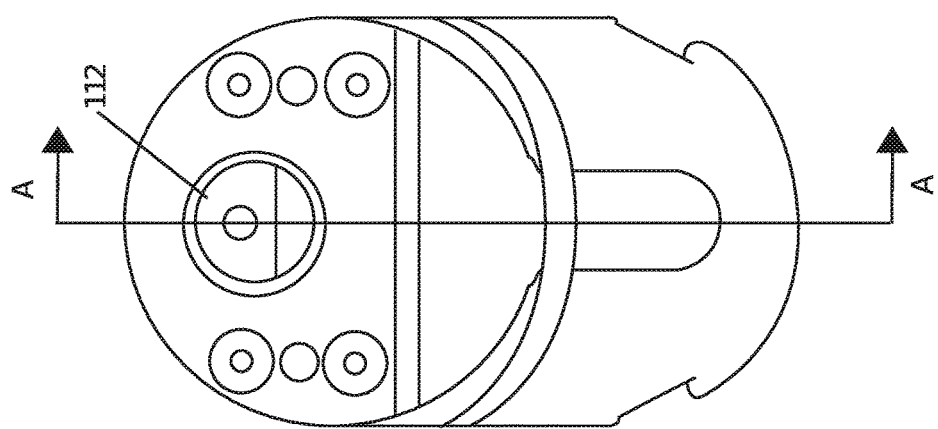
FIG. 16B shows an end view of a robotic shoulder, according to one embodiment.
Figure 16C:
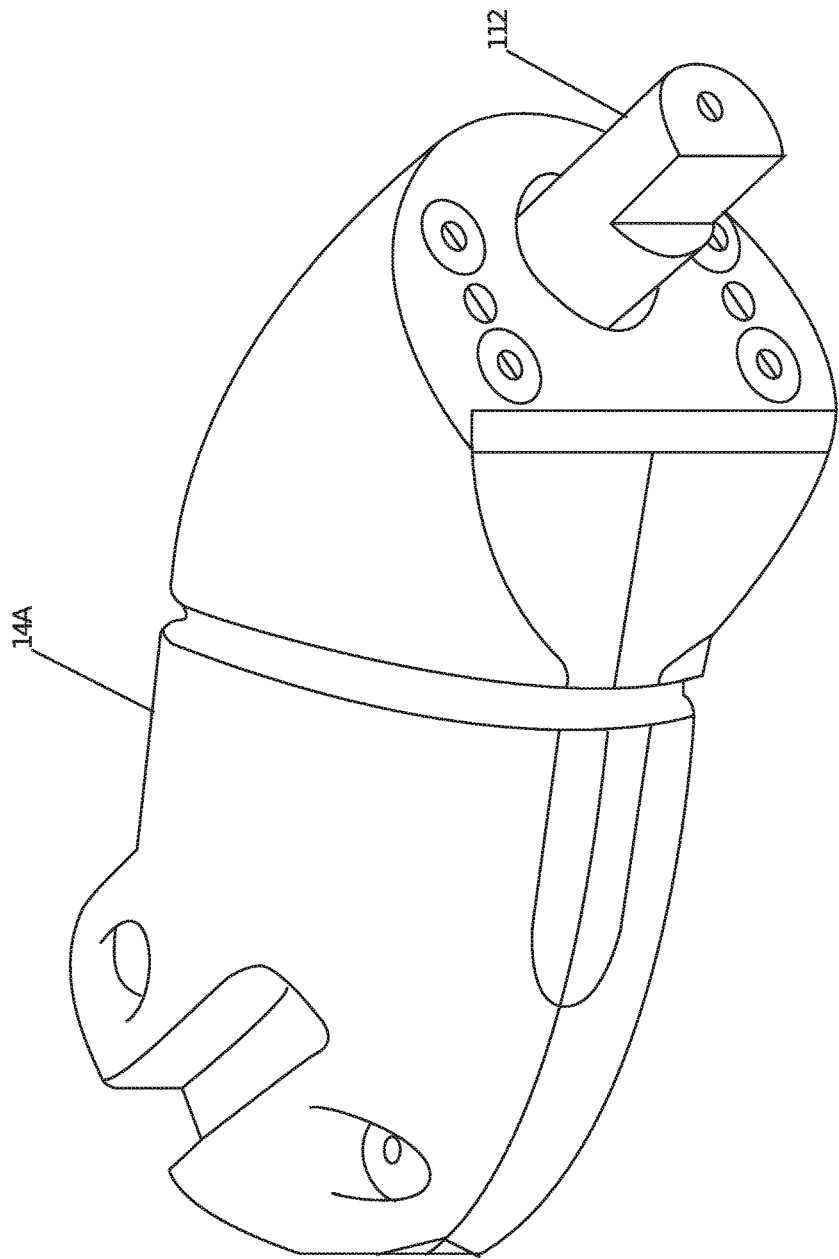
FIG. 16C shows a perspective view of a robotic shoulder, according to one embodiment.
Figure 16D:
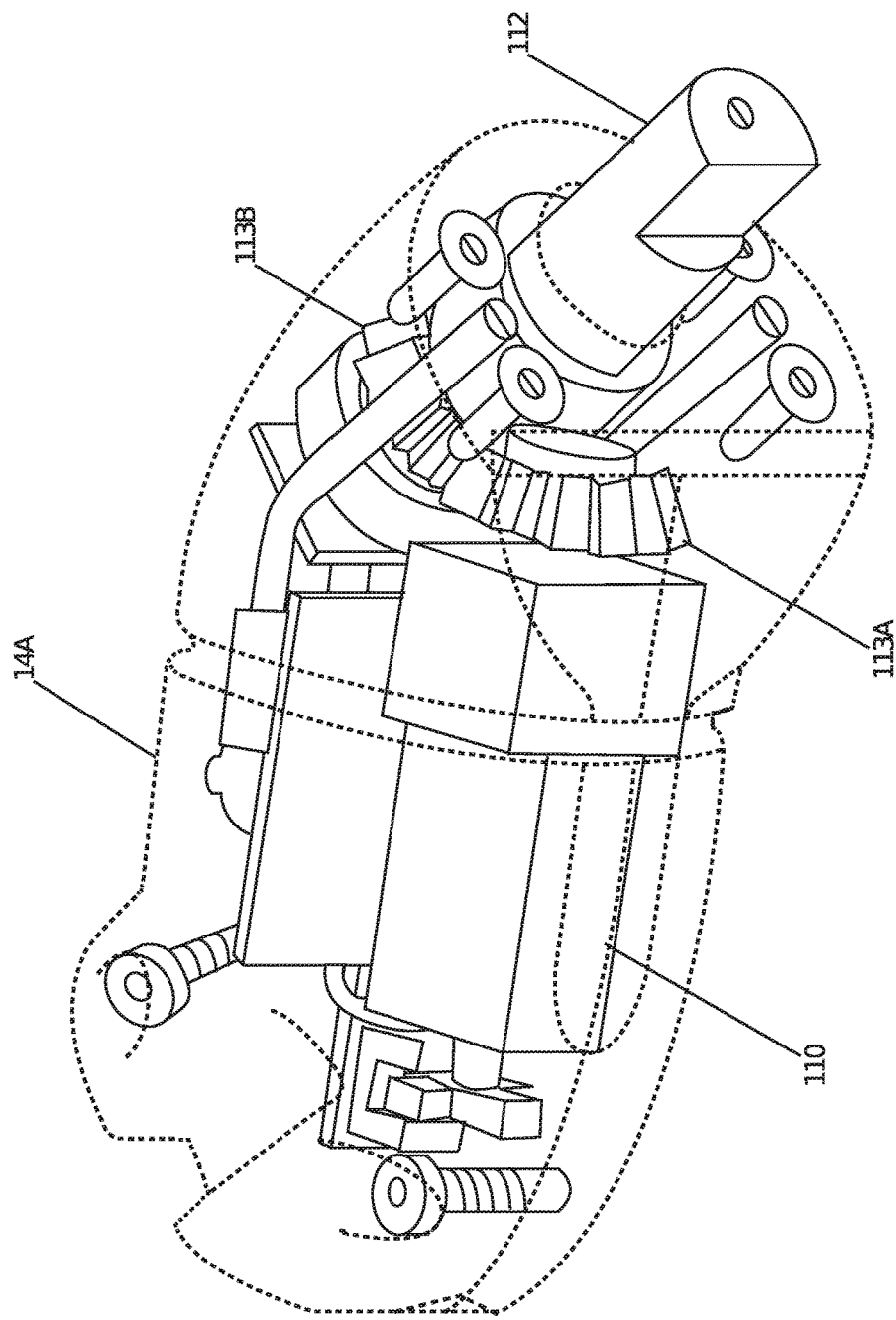
FIG. 16D shows a perspective cutaway view of a robotic shoulder, according to one embodiment.

FIGS. 13A-13D depict another embodiment of a forearm 90 for a robotic medical device. This embodiment shows an interchangeable operational component 92, which, in this specific example, is a grasper 92 commonly called a Babcock grasper. These interchangeable operational components can be similar to the interchangeable tools called Microline made by the Pentax Company. In this embodiment, as best shown in FIGS. 13B and 13C, the interchangeable tools are held in place using a known tapered collect device 94 (commonly used in machine tools) to hold the operational component in place. Here, the operational component is inserted into a tapered collect 94 that is then tightened in place using a threaded nut and a tapered slot 96. In this example, as best shown in FIG. 13D, there are two actuators 97, 98 that actuate open and closing of the operating component and rotation of the operating component (about axis DD as described above) by way of corresponding spur gears 97A, 98A with respect to the forearm 90. In this design, as an example, the operational component can be electrified for either mono-polar or bipolar cautery.

FIG. 14 shows how a fuse clip 100, or similar sliding contact device, can be used to provide an electrical connection to one or more portions of the operational component (not shown) to provide electricity for cautery. For example, as shown in the figure, the fuse clip 100 is coupled to a shaft 102 which may spin or rotate, the fuse clip 100 acting to maintain electrical connectivity to the shaft 102 for supply to the operational component (not shown) for cautery without the use of wires that may tangle and bunch. FIG. 14 also shows a printed circuit board (PCB) 114 that contains electronics to power and control the actuators as described previously. More specifically, in this particular figure, the PCB 114 is coupled to the actuator (not shown) such that it may control the electrification of the shaft 102 and ultimately the operational component (not shown).

FIGS. 15A-15D show one possible upper arm segment 16B embodiment. This segment 16B has two actuators 104, 106 that provide rotation of the forearm segment relative to the upper arm 16B and the upper arm 16B relative to the body 14, as described, for example, as axis CC and axis BB in FIG. 3, respectively. In this design, the two actuators 104, 106 are operably coupled to bevel gears 104A, 106A by way of drive gears 104B, 106B to change the axis of rotation of the motors 104, 106 by ninety degrees and make the two axes of rotation (CC & BB) perpendicular to the axes of the segment 16B. Also shown are the sensors and electronics used to control the segment 16B as described above.

FIGS. 16A-16D show one possible device body segment 14A embodiment. Here, an actuator 110 is coupled to the output shaft 112 by bevel gears 113A, 113B such that the axis of actuator 110 rotation is approximately 30 degrees from the axis of rotation of the output shaft 112. Also shown are the sensors and electronics used to control the actuator 110 in the body segment 14A in a fashion similar to that described above.

Figure 17B:
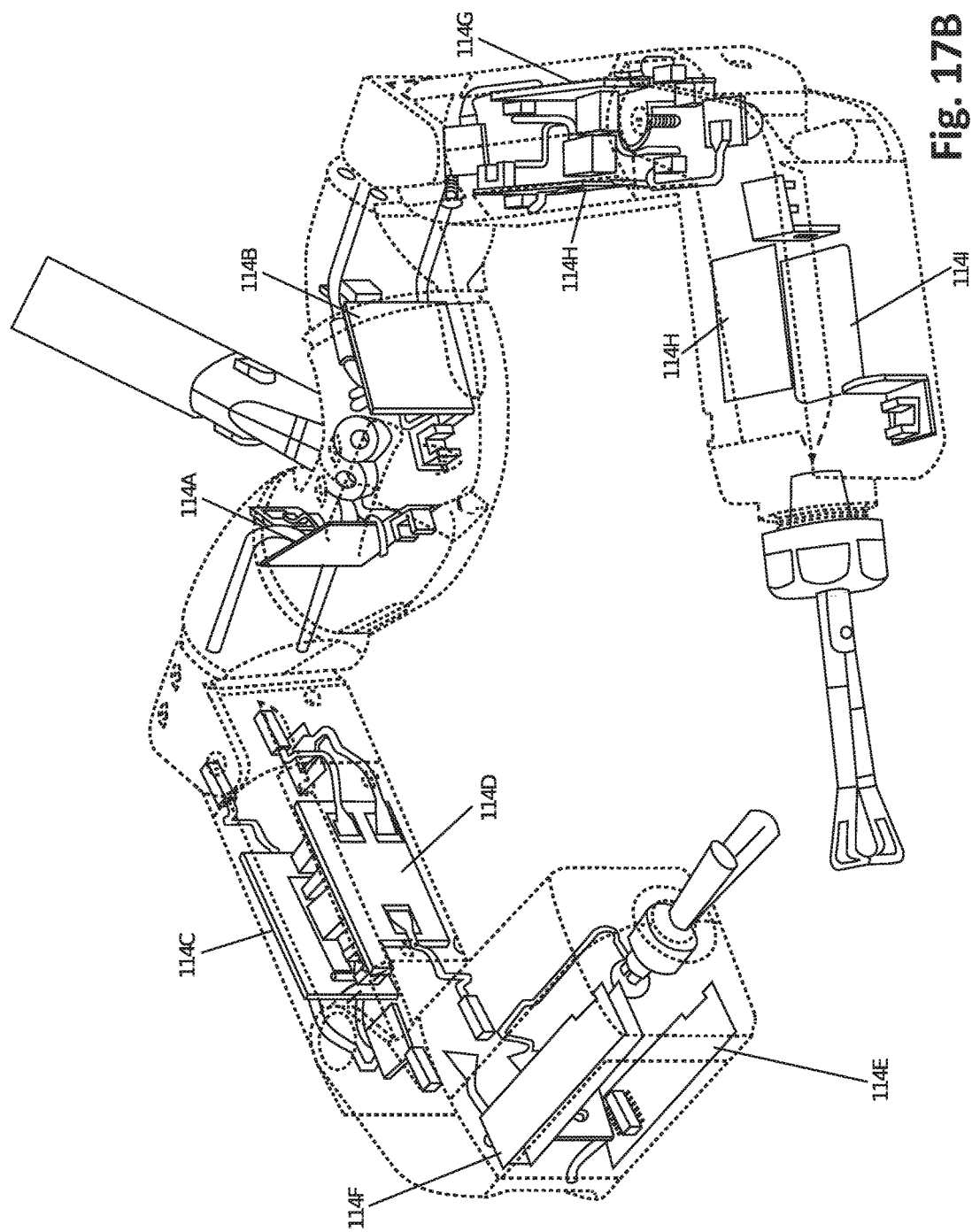
FIG. 17B shows a cutaway perspective view of robotic device circuit boards, according to one embodiment.

FIGS. 17A and 17B depict one possible implementation of a device 10 having printed circuit boards 114A-J and connective electrical cables 116A-J that are contained and routed inside the device 10 to provide electrical power and control. More specifically, FIG. 17A depicts the cables 116A-116J and FIG. 17B depicts the PCBs 114A-114J. In this example, "service loops" are provided at each joint to allow for relative motion between the links while not placing the cables in excessive bending or tension (not shown). Alternatively, the circuit boards and cabling can be positioned outside the robot.

Figure 18:
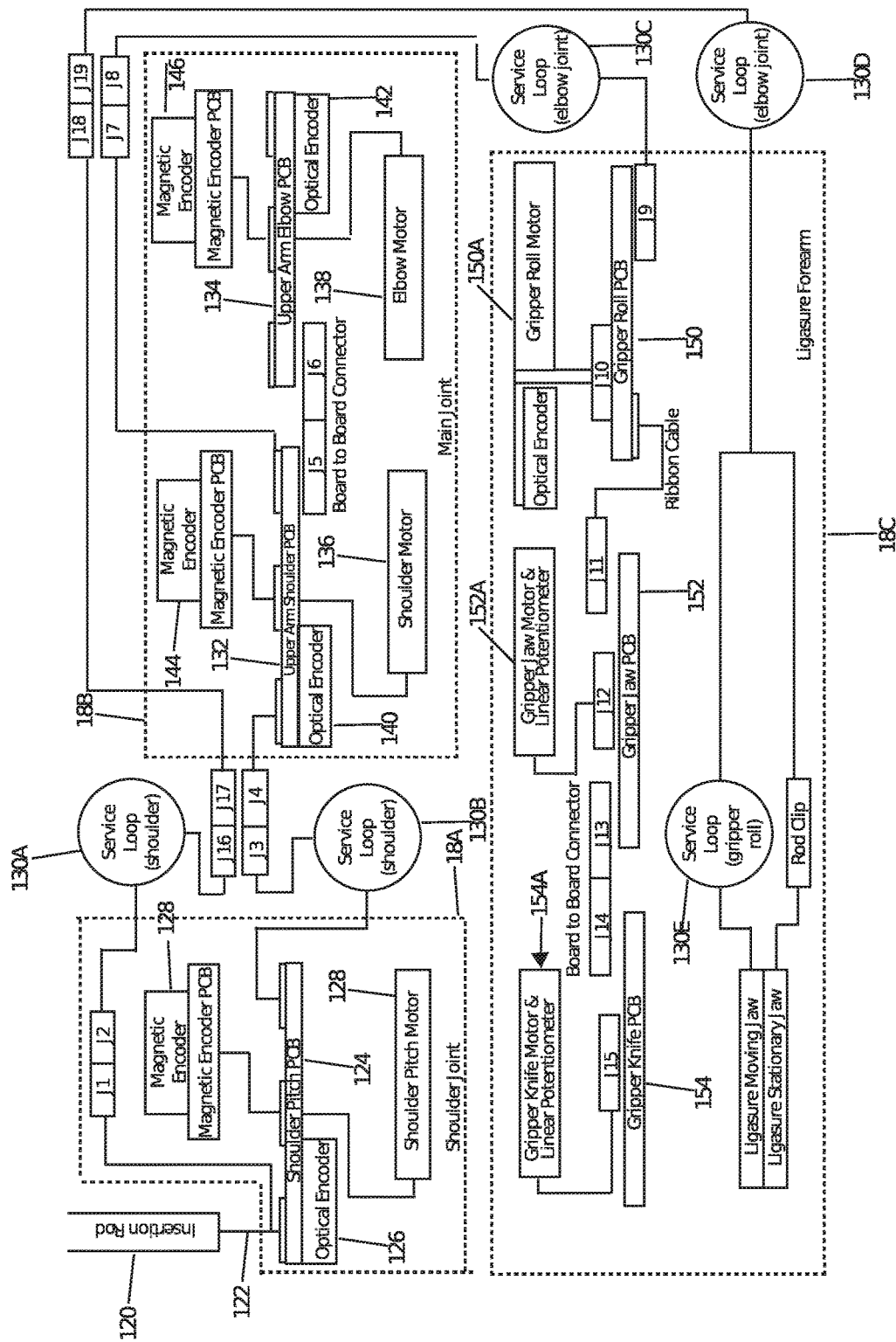
FIG. 18 shows a block diagram of electronics for a robotic device/arm, according to one embodiment.

FIG. 18 shows a general schematic for one possible design of the electrical sub-system of a robotic device in accordance with one embodiment. The schematic shows an example of the electronics for a vessel sealing arm, such as, for example, the right arm in the robot 10 depicted in FIGS. 2A and 2B. In this example as shown schematically in FIG. 18, the connection cable 122 enters through the support rod 120. This cable 122 can contain conductors for electrical power and electrical signals and other wires of various forms as required for operation of the device 10. This cable 122 interfaces with the shoulder pitch PCB 124. This shoulder pitch PCB 124 supports both an optical encoder 126 and a magnetic encoder 128 for redundant measurement of rotation of the first shoulder joint 18A (around axis AA) as shown in FIGS. 2A and 2B. This PCB 124 provides power to the shoulder pitch motor 128 (for rotation around axis AA). It can also be seen that the cable 122 (via connectors J1 and J2) passes via a service loop 130 into the main joint 18B (described as the upper arm above). Here a "service loop" 130A, 130B, 130C, 130D, 130E is provided at each joint to allow for relative motion between the links while not placing the cables in excessive bending or tension.

The shoulder pitch PCB is also connected to the upper arm via a service loop 130B and connectors (J3 & J4). In the upper arm 18B there is an upper arm shoulder PCB 132 (for axis BB in FIG. 2B) and an upper arm elbow PCB 134 (for axis CC). This link also has internal connectors J5 & J6. All connectors generally aid and allow for assembly and repair. Both PCBs 132, 134 in this link power an actuator 136, 138 for each joint (axis BB & CC) as well as both optical 140, 142 and magnetic 144, 146 encoders to measure joint position. The sensors in this arm and throughout the robot can be used redundantly and or individually or in combination. They can be either relative or absolute or in any combination. There are also connections from the upper arm to the lower arm via connectors listed as J7, J8, J18 & J19 and via service loops.

Here and throughout the robot service loops may or may not be required. The forearm contains three PCBs 150, 152, 154 to drive/control the gripper cutting device 154A, the gripper jaws 152A and the gripper roll 150A (axis DD). As before various sensors 156 and motors 150A, 152A, 154A are powered and used with the PCBs and various service loops 130C, 130D, 130E are used. As shown previously, the gripper can be electrified for cautery with one or more clips or connectors (or with a direct connection) that may or may not allow relative motion of the gripper jaws (axis DD). This example design shows a PCB for each joint. Alternatively a PCB could be used for each link, or each arm, or any combination of the above. The description above and shown in FIG. 21 is just one example of the electrical design that is possible.

Figure 19:
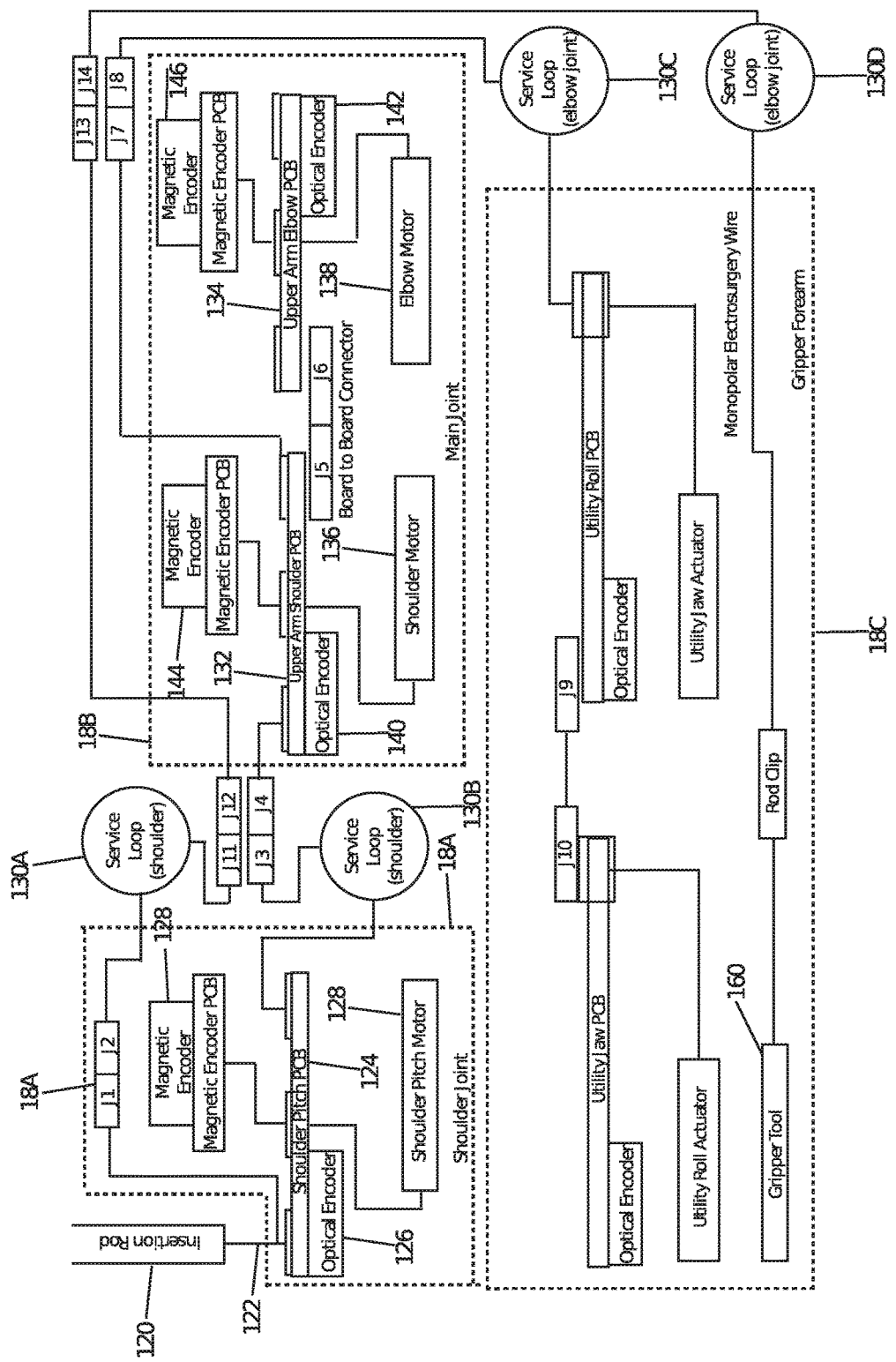
FIG. 19 shows a block diagram of electronics for a robotic device/arm, according to one embodiment.

FIG. 19 shows a general schematic for yet another possible design of the electrical sub system of the robotic device. The schematic in FIG. 19 shows an example of the electronics for an arm with interchangeable tools, also referred to as the utility arm or left arm 18 in the design of FIGS. 2A-2B. In this example the electronics, PCBs, connectors, and service loops, etc are similar to the schematic described in FIG. 18 but this arm does not have a cutting device and hence does not have on actuator and supporting mechanical and electrical components. Again, as shown previously, the gripper can be electrified for cautery with one or more clips or connectors (or with a direct connection) that may or may not allow relative motion of the gripper jaws (axis DD).

Again, in this version both operating components (vessel sealing and interchangeable Babcock grasper) can be electrified for cautery. In general any and combination of the operating components can be electrified with either no cautery, mono-polar cautery, bi-polar cautery, or other surgical treatment technique.

The robotic surgical device described here can be either single use and be designed to be disposed of after its use, or can be made so it can be re-used and sterilized between uses. In one embodiment, to ease cleaning of the device between uses, a protective sleeve is disclosed here that covers the majority of the outer surfaces of the robotic device.

According to one embodiment, shown in FIGS. 20A-20B, a dip mold pattern 200 (best shown in FIG. 20B) is created with a shape and size that is similar to the robotic arm 202 (best shown in FIG. 20A) (also called a utility arm or ligisure arm or other arm, for example 16, 18 in FIGS. 2A-2B) for which a protective sleeve is needed. The dip mold pattern 200 is designed in such a way as to be thicker and larger than the arm 202 in specific areas, such as, for example, around the joints 201A-D. This larger size will result in a protective sleeve 200 that is larger in these areas so it will provide slack for the robotic arm 202 to articulate.

Also, according to one embodiment, FIG. 20A shows how features 204A, 204B (or "grooves") are designed into the robotic device 202. In this embodiment, one groove 204A is at the proximal end of the robotic arm 202 and a second 204B is at the distal end of the arm 202. These grooves 204A, 204B are designed so the protective sleeve 200 will form a tight seal and mechanical connection with the robotic arm 202 to make the arm fluidically sealed.

In another embodiment, a mold, grooves, and sleeve could be created at each the proximal and distal ends of the joints so smaller protective sleeves would be created that would only cover the joint areas. Other combinations are also possible. For example one sleeve could cover two proximal joints and a second sleeve could cover a distal joint.

Figure 21A:
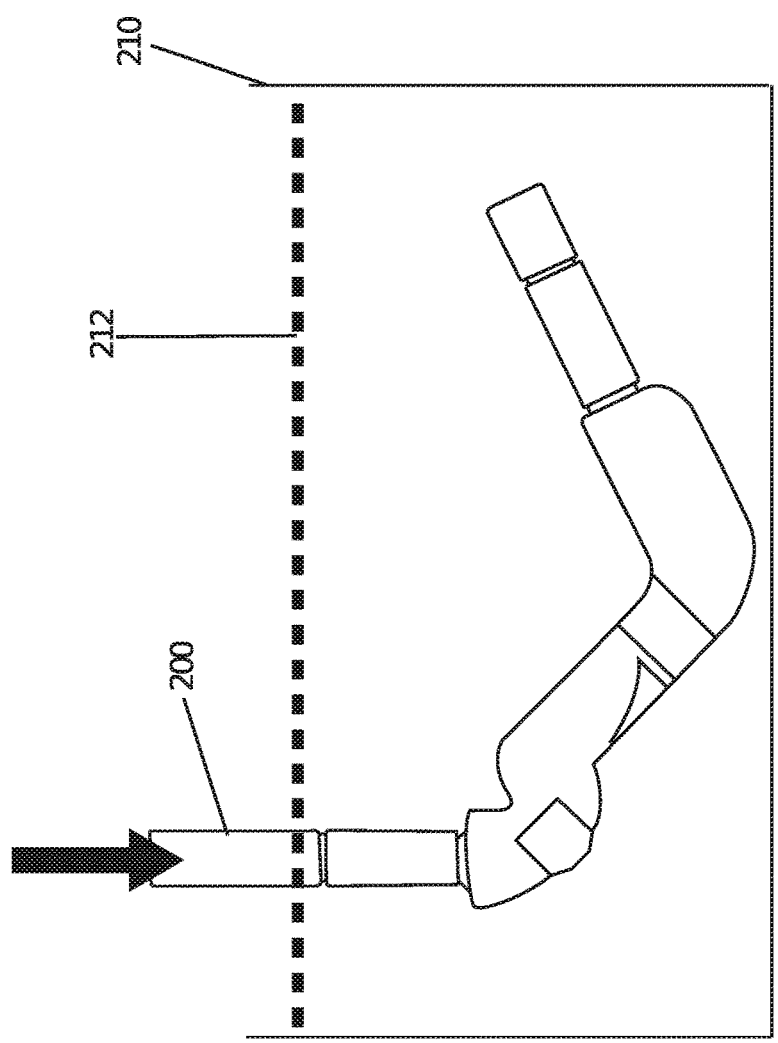
FIG. 21A shows a robotic arm and sleeve making process overview, according to one embodiment.
Figure 21B:
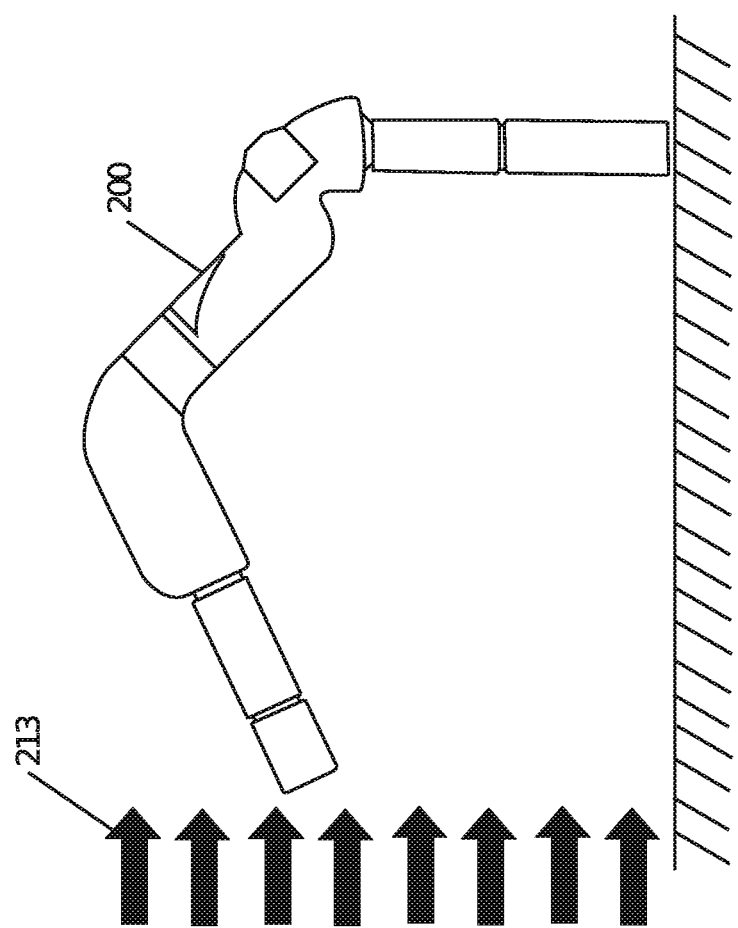
FIG. 21B shows a robotic arm and sleeve making process overview, according to one embodiment.

In use according to one embodiment as shown in FIGS. 21A and 21B, the dip mold pattern 200 can be placed into a vat 210 of dip mold material 212. In one embodiment, this mold material 212 could be a latex or similar material. The pattern can then be removed from the vat 210 and the mold material 212 is then cured in a heated oven 213. The process can be repeated to create multiple layers and thereby a thicker sleeve.

Figure 22A:
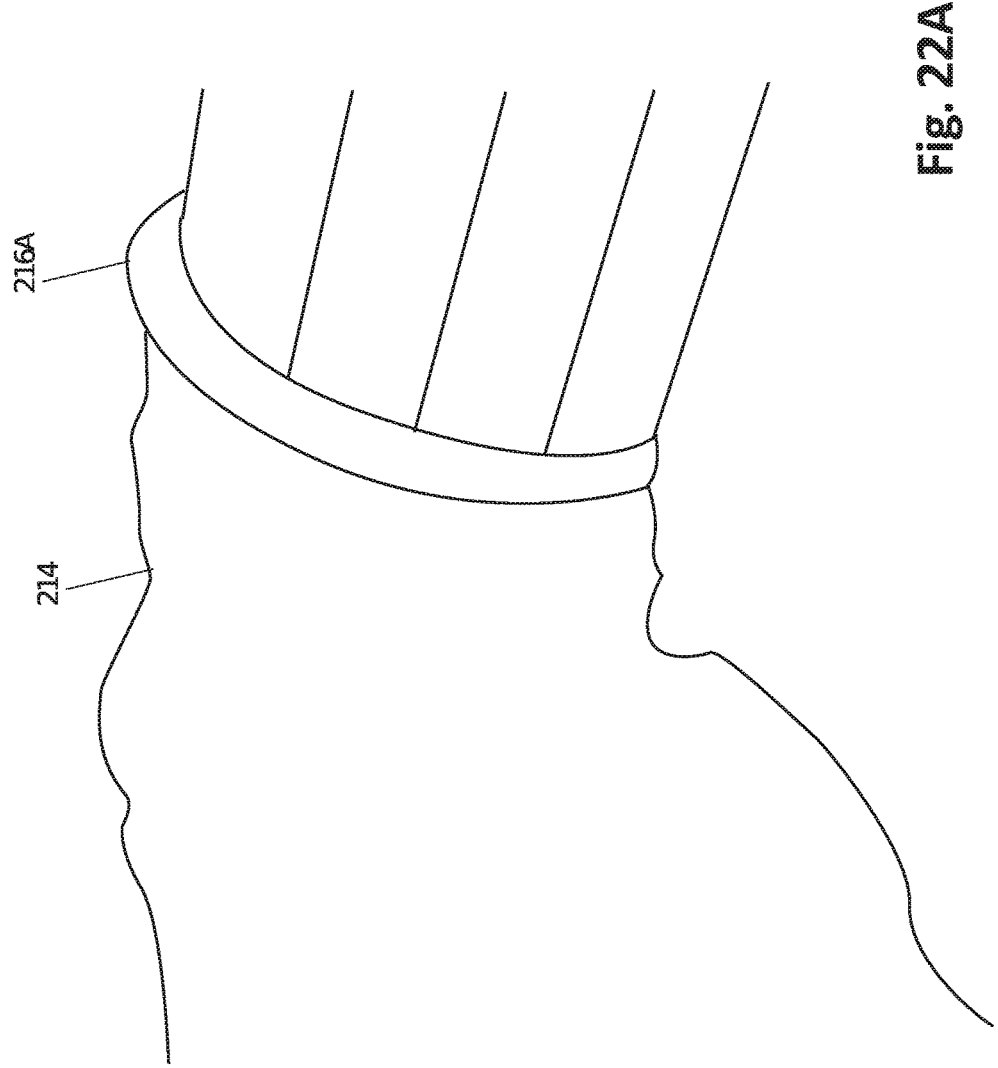
FIG. 22A shows the rolled edge of the protective sleeve and the sleeve placed on the robotic arm, according to one embodiment.
Figure 22B:
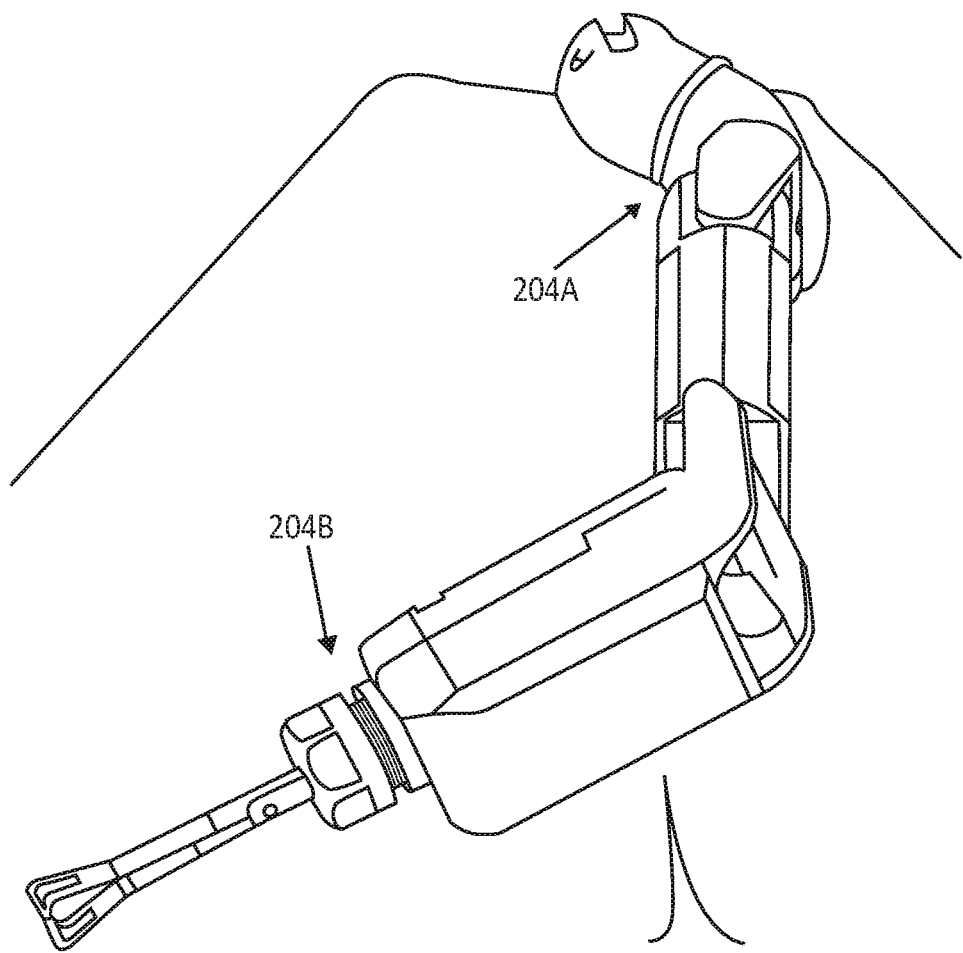
FIG. 22B shows the robotic arm, according to one embodiment.

When the mold material is cured, according to one embodiment and shown in FIGS. 22A and 22B, the resulting protective sleeve 214 can be trimmed at each end and then the ends can be rolled 216A, 216B. Rolling the ends creates "beads" at both the proximal 216A and distal 216B ends of the protective sleeve. These "beads" 216A, 216B are designed to fit in the grooves 204A, 204B or other external features or contours (shown as an example in FIG. 20) on the robotic device. The sleeve 214 is then removed from the dip mold 200 and placed onto the robotic arm 202. It can be seen how the protective sleeve 214 now covers and protects most or all of the robotic arm 202 (including the moving joints) from fluid ingress during surgery.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

We claim:

1. A modular surgical robotic system, comprising:
 a. a modular robotic device sized to be positioned completely within a patient further comprising:
  i. a body component further comprising a first shoulder component and a second shoulder component;
  ii. a first movable segmented robotic arm comprising a housing with at least one motor disposed within the housing and operationally connected to the body component by way of the first shoulder component;
  iii. a second movable segmented robotic arm comprising a housing with at least one motor disposed within the housing and operationally connected to the body component by way of the second shoulder component;
  iv. a first operational component operationally connected to the first robotic arm; and
  v. a second operational component operationally connected to the second robotic arm;
 b. a port configured for traversing the body of a patient;
 c. a support rod for crossing the port from the interior to exterior of the patient and connecting to the first and second body components; and
 d. an operations system for control of the modular robotic device from outside the patient by way of the port and support rod, the operations system in electrical communication with the modular robotic device.

2. The modular surgical robotic system of claim 1, wherein the modular robotic device may be assembled within the body cavity of the patient.

3. The modular surgical robotic system of claim 2, wherein the support rod is further comprised of a first support rod segment and a second support rod segment.

4. The modular surgical robotic system of claim 3, wherein the first support rod component and second support rod component are rotationally coupled to the first shoulder component and second shoulder component, respectively.

5. The modular surgical robotic system of claim 4, wherein the support rod is substantially enclosed in an overtube.

6. The modular surgical robotic system of claim 1, wherein the body component is cylindrical.

7. The modular surgical robotic system of claim 1, wherein the first shoulder component and second shoulder component are set at an obtuse angle from one another.

8. The modular surgical robotic system of claim 1, wherein the first operational component is chosen from a group consisting of a grasping component, a cauterizing component, a suturing component, an imaging component, an operational arm component, a sensor component, and a lighting component.

9. The modular surgical robotic system of claim 1, wherein the second operational component is chosen from a group consisting of a grasping component, a cauterizing component, a suturing component, an imaging component, an operational arm component, a sensor component, and a lighting component.

10. The modular surgical robotic system of claim 1, further comprising one or more motors for operation, rotation or movement of at least one of the first shoulder, the second shoulder, the first segmented arm, the second segmented arm, the first operational component, and the second operational component.

11. The modular surgical robotic system of claim 1, wherein the port creates an insufflation seal in the body.

12. A modular surgical robotic system, comprising:
   a. a modular robotic device sized to be positioned completely within a patient further comprising:
      i. a first shoulder component;
      ii. a second shoulder component;
      iii. a body component, formed by the connection of the first shoulder component to the second shoulder component;
      iv. a first movable segmented robotic arm comprising at least one motor and operationally connected to the body component by way of the first shoulder component;
      v. a second movable segmented robotic arm comprising at least one motor and operationally connected to the body component by way of the second shoulder component;
      vi. a first operational component operationally connected to the first robotic arm; and
      vii. a second operational component operationally connected to the second robotic arm;
   b. a port configured for traversing the body of a patient; and
   c. an operations system for control of the modular robotic device from outside the patient by way of the port and support rod, the operations system in electrical communication with the modular robotic device.

13. The modular surgical robotic system of claim 12, wherein the body component is cylindrical.

14. The modular surgical robotic system of claim 12, wherein the first shoulder component and second shoulder component are set at an obtuse angle from one another.

15. The modular surgical robotic system of claim 12, wherein the first operational component is chosen from a group consisting of a grasping component, a cauterizing component, a suturing component, an imaging component, an operational arm component, a sensor component, and a lighting component.

16. The modular surgical robotic system of claim 12, wherein the second operational component is chosen from a group consisting of a grasping component, a cauterizing component, a suturing component, an imaging component, an operational arm component, a sensor component, and a lighting component.

17. The modular surgical robotic system of claim 12, further comprising one or more motors for operation, rotation or movement of at least one of the first shoulder, the second shoulder, the first segmented arm, the second segmented arm, the first operational component, and the second operational component.

18. The modular surgical robotic system of claim 12, wherein the port is constructed and arranged to create an insufflation seal in the body of the patient.

19. The modular surgical robotic system of claim 12, wherein the modular robotic device may be assembled within the body cavity of the patient.

\* \* \* \* \*